(12) United States Patent
Schilowitz et al.

(10) Patent No.: US 9,926,509 B2
(45) Date of Patent: Mar. 27, 2018

(54) LUBRICATING OIL COMPOSITIONS WITH ENGINE WEAR PROTECTION AND SOLUBILITY

(71) Applicant: ExxonMobil Research and Engineering Company, Annandale, NJ (US)

(72) Inventors: Alan M. Schilowitz, Highland Park, NJ (US); Man Kit Ng, Basking Ridge, NJ (US); David J. Baillargeon, Cherry Hill, NJ (US); Chen Chen, State College, PA (US); Harry R. Allcock, State College, PA (US); Andrew R. Hess, York, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 33 days.

(21) Appl. No.: 14/997,808

(22) Filed: Jan. 18, 2016

(65) Prior Publication Data
US 2016/0208186 A1 Jul. 21, 2016

Related U.S. Application Data

(60) Provisional application No. 62/104,958, filed on Jan. 19, 2015.

(51) Int. Cl.
*C10M 137/00* (2006.01)
*C10M 137/16* (2006.01)
(Continued)

(52) U.S. Cl.
CPC ....... *C10M 137/16* (2013.01); *C07F 9/65815* (2013.01); *C10M 107/02* (2013.01);
(Continued)

(58) Field of Classification Search
CPC .............. C10M 137/16; C10M 107/02; C10M 137/10; C10M 169/04; C10M 2203/1006;
(Continued)

(56) References Cited

U.S. PATENT DOCUMENTS 1,815,022 A 7/1931 Davis
2,015,748 A 10/1935 Frolich
(Continued)

FOREIGN PATENT DOCUMENTS

CA 1094044 A 1/1981
EP 0464546 A1 6/1991
(Continued)

*Primary Examiner* — Cephia D Toomer
(74) *Attorney, Agent, or Firm* — Robert A. Migliorini

(57) ABSTRACT

A method for improving wear control in an engine or other mechanical component lubricated with a lubricating oil by using as the lubricating oil a formulated oil. The formulated oil has a composition that includes a lubricating oil base stock as a major component; and at least one phosphazene represented by the formula

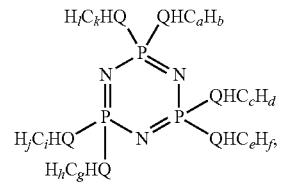

as a minor component. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value
(Continued)

| Candidate Formulation | Phosphazene Concentration | Average Friction (at end of 2 hour test) | Wear Scar Depth (angstroms) |
|---|---|---|---|
| Partial Formulation + Phosphazene Formula 1 | 1.5 weight % | 0.174 | 2062 |
| Partial Formulation + Phosphazene Formula 2 | 1.5 weight % | 0.163 | 3701 |
| Partial Formulation + Phosphazene Formula 3 | 1.5 weight % | .165 | 6623 |
| Partial Formulation (No Friction Modifier or Antiwear) | | 0.15 | 30000 |
| Full Formulation | | 0.08 | 7500 | of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. A lubricating oil having a composition that includes a lubricating oil base stock as a major component; and at least one phosphazene represented by the above formula as a minor component. The lubricating oil is useful in internal combustion engines.

32 Claims, 1 Drawing Sheet

(51) Int. Cl.
  C10M 107/02 (2006.01)
  C10M 137/10 (2006.01)
  C10M 169/04 (2006.01)
  C07F 9/6593 (2006.01)
(52) U.S. Cl.
  CPC ........ *C10M 137/10* (2013.01); *C10M 169/04* (2013.01); *C10M 2203/1006* (2013.01); *C10M 2203/1025* (2013.01); *C10M 2205/0285* (2013.01); *C10M 2223/045* (2013.01); *C10M 2223/08* (2013.01); *C10N 2230/06* (2013.01); *C10N 2230/43* (2013.01); *C10N 2230/54* (2013.01); *C10N 2240/10* (2013.01)
(58) Field of Classification Search
  CPC .. C10M 2203/1025; C10M 2205/0285; C10M 2223/045; C10M 2223/08; C07F 9/65815; C10N 2230/06; C10N 2230/43; C10N 2230/54; C10N 2240/10
  See application file for complete search history.

(56) References Cited

U.S. PATENT DOCUMENTS

| | | |
|---|---|---|
| 2,100,993 A | 11/1937 | Bruson |
| 2,191,498 A | 2/1940 | Reiff |
| 2,387,501 A | 10/1945 | Dietrich |
| 2,655,479 A | 10/1953 | Munday et al. |
| 2,666,746 A | 1/1954 | Munday et al. |
| 2,721,877 A | 10/1955 | Popkin et al. |
| 2,721,878 A | 10/1955 | Popkin |
| 2,817,693 A | 12/1957 | Koome et al. |
| 3,036,003 A | 5/1962 | Verdol |
| 3,087,936 A | 4/1963 | Le Suer |
| 3,172,892 A | 3/1965 | Le Suer et al. |
| 3,200,107 A | 8/1965 | Le Suer |
| 3,215,707 A | 11/1965 | Rense |
| 3,219,666 A | 11/1965 | Norman et al. |
| 3,250,715 A | 5/1966 | Wyman |
| 3,254,025 A | 5/1966 | Le Suer |
| 3,272,746 A | 9/1966 | Le Suer et al. |
| 3,275,554 A | 9/1966 | Wagenaar |
| 3,322,670 A | 5/1967 | Burt et al. |
| 3,329,658 A | 7/1967 | Fields |
| 3,316,177 A | 8/1967 | Dorer, Jr. |
| 3,341,542 A | 9/1967 | Le Suer et al. |
| 3,382,291 A | 5/1968 | Brennan |
| 3,413,347 A | 11/1968 | Worrel |
| 3,438,757 A | 4/1969 | Honnen et al. |
| 3,444,170 A | 5/1969 | Norman et al. |
| 3,449,250 A | 6/1969 | Fields |
| 3,454,555 A | 7/1969 | van der Voort et al. |
| 3,454,607 A | 7/1969 | Le Suer et al. |
| 3,519,565 A | 7/1970 | Coleman |
| 3,541,012 A | 11/1970 | Stuebe |
| 3,565,804 A | 2/1971 | Honnen et al. |
| 3,595,791 A | 7/1971 | Cohen |
| 3,630,904 A | 12/1971 | Musser et al. |
| 3,632,511 A | 1/1972 | Liao |
| 3,652,616 A | 3/1972 | Watson et al. |
| 3,666,730 A | 5/1972 | Coleman |
| 3,687,849 A | 8/1972 | Abbott |
| 3,697,574 A | 10/1972 | Piasek et al. |
| 3,702,300 A | 11/1972 | Coleman |
| 3,703,536 A | 11/1972 | Piasek et al. |
| 3,704,308 A | 11/1972 | Piasek et al. |
| 3,725,277 A | 4/1973 | Worrel |
| 3,725,480 A | 4/1973 | Traise et al. |
| 3,726,882 A | 4/1973 | Traise et al. |
| 3,742,082 A | 6/1973 | Brennan |
| 3,751,365 A | 8/1973 | Piasek et al. |
| 3,755,433 A | 8/1973 | Miller et al. |
| 3,756,953 A | 9/1973 | Piasek et al. |
| 3,769,363 A | 10/1973 | Brennan |
| 3,787,374 A | 1/1974 | Adams |
| 3,798,165 A | 3/1974 | Piasek et al. |
| 3,803,039 A | 4/1974 | Piasek et al. |
| 3,822,209 A | 7/1974 | Knapp et al. |
| 3,876,720 A | 4/1975 | Heilman et al. |
| 3,948,800 A | 4/1976 | Meinhardt |
| 4,100,082 A | 7/1978 | Clason et al. |
| 4,149,178 A | 4/1979 | Estes |
| 4,218,330 A | 8/1980 | Shubkin |
| 4,234,435 A | 11/1980 | Meinhardt et al. |
| 4,239,930 A | 12/1980 | Allphin et al. |
| 4,367,352 A | 1/1983 | Watts, Jr. et al. |
| 4,413,156 A | 11/1983 | Watts, Jr. et al. |
| 4,426,305 A | 1/1984 | Malec |
| 4,434,408 A | 2/1984 | Baba et al. |
| 4,454,059 A | 6/1984 | Pindar et al. |
| 4,594,172 A | 6/1986 | Sie |
| 4,767,551 A | 8/1988 | Hunt et al. |
| 4,798,684 A | 1/1989 | Salomon |
| 4,827,064 A | 5/1989 | Wu |
| 4,827,073 A | 5/1989 | Wu |
| 4,897,178 A | 1/1990 | Best et al. |
| 4,910,355 A | 3/1990 | Shubkin et al. |
| 4,921,594 A | 5/1990 | Miller |
| 4,943,672 A | 7/1990 | Hamner et al. |
| 4,952,739 A | 8/1990 | Chen |
| 4,956,122 A | 9/1990 | Watts et al. |
| 4,975,177 A | 12/1990 | Garwood et al. |
| 5,068,487 A | 11/1991 | Theriot |
| 5,073,284 A | 12/1991 | Klobucar et al. |
| 5,084,197 A | 1/1992 | Galic et al. |
| 5,105,001 A * | 4/1992 | Goins ................. C07F 9/65815 558/80 |
| 5,194,652 A | 3/1993 | Nader |
| 5,430,105 A | 7/1995 | Redpath et al. |
| 5,705,458 A | 1/1998 | Roby et al. |
| 5,908,817 A | 6/1999 | Perettie et al. |
| 6,034,039 A | 3/2000 | Gomes et al. |
| 6,080,301 A | 6/2000 | Berlowitz et al. |
| 6,090,989 A | 7/2000 | Trewella et al. |
| 6,165,949 A | 12/2000 | Berlowitz et al. |
| 6,323,164 B1 | 11/2001 | Liesen et al. |
| 6,608,009 B2 | 8/2003 | Akada et al. |
| 7,025,609 B2 | 4/2006 | Matsumoto et al. |
| 7,704,930 B2 | 4/2010 | Deckman et al. |
| 8,048,833 B2 | 11/2011 | Habeeb et al. |
| 2008/0020950 A1 | 1/2008 | Gray et al. |
| 2009/0318664 A1 | 12/2009 | Yang et al. |
| 2011/0064970 A1 | 3/2011 | Chen et al. |

FOREIGN PATENT DOCUMENTS

| | | |
|---|---|---|
| EP | 0464547 A1 | 6/1991 |
| EP | 0471071 B1 | 8/1995 |
| EP | 1873162 A1 | 1/2005 |
| GB | 1350257 A | 4/1974 |
| GB | 1390359 A | 4/1975 |
| GB | 1429494 A | 3/1976 |
| GB | 1440230 A | 6/1976 |

* cited by examiner

| Candidate Formulation | Phosphazene Concentration | Average Friction (at end of 2 hour test) | Wear Scar Depth (angstroms) |
|---|---|---|---|
| Partial Formulation + Phosphazene Formula 1 | 1.5 weight % | 0.174 | 2062 |
| Partial Formulation + Phosphazene Formula 2 | 1.5 weight % | 0.163 | 3701 |
| Partial Formulation + Phosphazene Formula 3 | 1.5 weight % | .165 | 6623 |
| Partial Formulation (No Friction Modifier or Antiwear) | | 0.15 | 30000 |
| Full Formulation | | 0.08 | 7500 |

LUBRICATING OIL COMPOSITIONS WITH ENGINE WEAR PROTECTION AND SOLUBILITY

CROSS-REFERENCE TO RELATED APPLICATIONS

This application claims priority to U.S. Provisional Application Ser. No. 62/104,958 filed Jan. 19, 2015, which is herein incorporated by reference in its entirety.

FIELD

This disclosure relates to a method for improving wear control in an engine or other mechanical component lubricated with a lubricating oil by including a phosphazene additive in low concentration in the lubricating oil. This disclosure also relates to a method for improving wear control, while maintaining solubility, in an engine or other mechanical component lubricated with a lubricating oil by including a phosphazene additive in low concentration in the lubricating oil. The lubricating oils of this disclosure are useful in internal combustion engines.

BACKGROUND

A major challenge in engine oil formulation is simultaneously achieving wear and deposit control, and oxidation stability, while also maintaining fuel economy performance, over a broad temperature range.

Lubricant-related wear control is highly desirable due to increasing use of low viscosity engine oils for improved fuel efficiency. As governmental regulations for vehicle fuel consumption and carbon emissions become more stringent, use of low viscosity engine oils to meet the regulatory standards is becoming more prevalent. At the same time, lubricants need to provide a substantial level of durability and wear protection due to the formation of thinner lubricant films during engine operation. As such, use of antiwear additives in a lubricant formulation is the typical method for achieving wear control and durability. Due to limitations of using high levels of some antiwears due to catalyst poisoning and deposit formation, it is highly desirable to find alternative methods for achieving excellent wear control and durability without poisoning the catalyst.

Most current antiwear additives contain metals, phosphorous and/or sulfur. Zinc dialkyl dithiophosphate (ZDDP) is a common antiwear additive used in engine lubricants. However, these elements are known to harm catalysts used to treat exhaust gases from internal combustion engines, and thus antiwear additives which are free of metals, sulfur and phosphorous will be advantaged in the marketplace.

It is also beneficial that additives used to improve lubricant performance form stable solutions or dispersions without rapidly dropping out.

Despite advances in lubricant oil formulation technology, there exists a need for a homogenous, compatible engine oil lubricant that effectively improves wear control while maintaining or improving fuel efficiency.

SUMMARY

This disclosure relates in part to a method for improving wear control in an engine or other mechanical component lubricated with a lubricating oil by including a soluble phosphazene additive in low concentration in the lubricating oil. This disclosure also relates to a method for improving wear control with a homogenous lubricant, while maintaining or improving fuel efficiency, in an engine or other mechanical component lubricated with a lubricating oil by including a soluble phosphazene additive in low concentration in the lubricating oil. The lubricating oils of this disclosure are useful in internal combustion engines.

This disclosure also relates in part to a method for improving wear control in an engine or other mechanical component lubricated with a lubricating oil by using as the lubricating oil a formulated oil. The formulated oil has a composition comprising a lubricating oil base stock as a major component; and at least one phosphazene represented by the formula

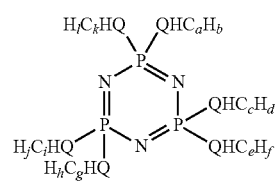

as a minor component. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. Wear control is improved as compared to wear control achieved using a lubricating oil containing a minor component other than the phosphazene.

In an embodiment, wear control is improved and solubility and fuel efficiency are maintained or improved as compared to wear control, solubility and fuel efficiency achieved using a lubricating oil containing a minor phosphazene component other than the phosphazene of this disclosure.

This disclosure further relates in part to a method for producing a stable lubricating oil formulation with improved wear control in an engine or other mechanical component lubricated with a lubricating oil by using as the lubricating oil a formulated oil. The formulated oil has a composition comprising a lubricating oil base stock as a major component; and at least one phosphazene represented by the formula

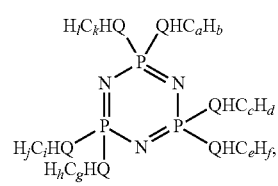

as a minor component. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. Wear control is improved as compared to wear control achieved using a lubricating engine oil containing a minor component other than the phosphazene.

In an embodiment, wear control is improved and solubility and fuel efficiency are maintained or improved as compared to wear control, solubility and fuel efficiency achieved using a lubricating oil containing a minor phosphazene component other than the phosphazene of this disclosure.

This disclosure further relates in part to a lubricating oil having a composition comprising a lubricating oil base stock as a major component; and at least one phosphazene represented by the formula

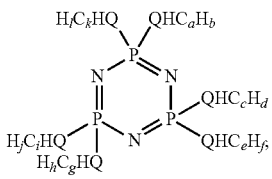

as a minor component. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. Wear control is improved as compared to wear control achieved using a lubricating oil containing a minor component other than the phosphazene.

In an embodiment, wear control is improved and solubility and fuel efficiency are maintained or improved as compared to wear control, solubility and fuel efficiency achieved using a lubricating oil containing a minor phosphazene component other than the phosphazene of this disclosure.

This disclosure yet further relates in part to a composition represented by the formula

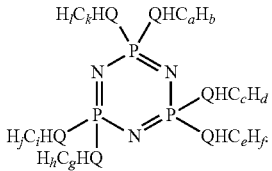

wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1.

This disclosure also relates in part to a process for preparing a composition represented by the formula

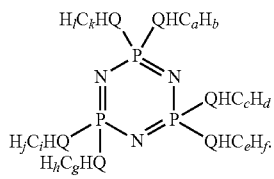

wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; said process comprising: reacting one or more alkylamines, thiols or alcohols and one or more phosphazene precursors in the presence of a solvent and under reaction conditions sufficient to prepare the composition represented by the above formula.

This disclosure further relates in part to a method for reducing sulfur and metals and their harmful side effects of exhaust catalyst poisoning and increased corrosivity in an engine or other mechanical component lubricated with a lubricating oil by including at least one phosphazene represented by the formula

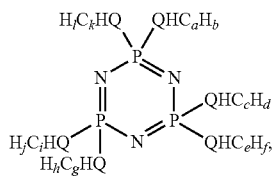

in the lubricating oil in a low concentration (e.g., an amount from about 0.01 weight percent to about 3 weight percent based on the total weight of the lubricating oil). In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1.

This disclosure yet further relates in part to a low sulfur, low metal lubricating oil having a composition comprising a lubricating oil base stock as a major component, and at least one phosphazene represented by the formula

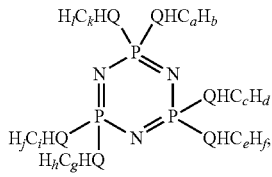

as a minor component. The at least one phosphazene is present in a low concentration (e.g., an amount from about 0.01 weight percent to about 3 weight percent based on the total weight of the lubricating oil). In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1.

It has been surprisingly found that, in accordance with this disclosure, improvements in wear control are obtained by including at least one phosphazene represented by the formula

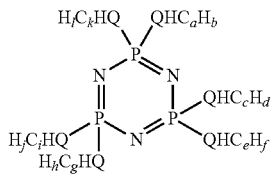

in the lubricating oil. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. The phosphazene additive affords greater improvements in wear control as compared to wear control achieved using a lubricating oil containing a minor component other than the phosphazene. In addition, wear control is improved and fuel efficiency is maintained or improved as compared to wear control and fuel efficiency achieved using a lubricating engine oil containing a minor component other than the phosphazene.

Further, it has been surprisingly found that phosphazenes with mixed substituent groups (e.g., a mixture of propyl and butyl groups) substituted on the phosphorus have improved solubility in hydrocarbon basestocks (e.g., PAO), and form stable lubricant blends without rapidly dropping out.

Other objects and advantages of the present disclosure will become apparent from the detailed description that follows.

BRIEF DESCRIPTION OF THE DRAWINGS

FIG. 1 shows High Frequency Reciprocating Rig (HFRR) testing results, in particular average friction and wear scar depth, for formulations in accordance with Example 1.

DETAILED DESCRIPTION

All numerical values within the detailed description and the claims herein are modified by "about" or "approximately" the indicated value, and take into account experimental error and variations that would be expected by a person having ordinary skill in the art.

It has now been found that improved wear control can be attained in an engine or other mechanical component lubricated with a lubricating oil by using as the lubricating oil a formulated oil that has at least one phosphazene represented by the formula

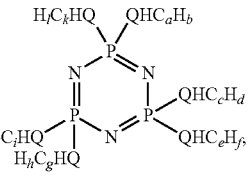

in the lubricating oil. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. Wear control is improved as compared to wear control achieved using a lubricating oil containing a minor component other than the phosphazene.

The formulated oil preferably comprises a lubricating oil base stock as a major component, and at least one phosphazene represented by the formula

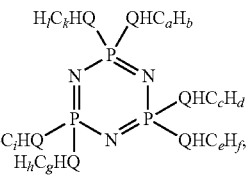

as a minor component. In the above formula, Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. The lubricating oils of this disclosure are particularly advantageous as passenger vehicle engine oil (PVEO) products.

In an embodiment, wear control is improved and solubility and fuel efficiency are maintained or improved as compared to wear control, solubility and fuel efficiency achieved using a lubricating engine oil containing a minor phosphazene component other than the phosphazene of this disclosure.

In accordance with this disclosure, it has been found that certain substituted phosphazene trimers have unexpected wear benefits when blended at low dosage into hydrocarbon lubricants. In addition, while many phosphazenes are not very soluble in hydrocarbon lubricants, this disclosure includes phosphazene structures that are soluble in hydrocarbons and form clear solutions in hydrocarbon basestocks.

In another embodiment, wear control is improved and fuel efficiency is maintained or improved in low viscosity lubricants (e.g., 0W-16, 0W-12, 0W-8, 0W-4, 0W-0, and the like).

In addition, the lubricating oils of this disclosure can be useful as commercial vehicle engine oil products (e.g., heavy duty lubricants). In particular, the lubricating oils of this disclosure can be useful for reducing wear in high soot content lubricants and diesel oils.

The lubricating oils of this disclosure provide excellent engine or other mechanical component protection including antiwear performance. This benefit can be demonstrated for the lubricating oils of this disclosure in engine tests. The lubricating oils of this disclosure provide improved fuel efficiency. A lower viscosity engine oil generally provides superior fuel economy to a higher viscosity product.

The lubricating engine oils of this disclosure can have a composition sufficient to pass wear protection requirements of one or more engine tests.

The present disclosure provides lubricant compositions with excellent antiwear properties. Antiwear additives are generally required for reducing wear in operating equipment where two solid surfaces engage in contact. In the absence of antiwear chemistry, the surfaces can rub together causing material loss on one or both surfaces which can eventually lead to equipment malfunction and failure. Antiwear additives can produce a protective surface layer which reduces wear and material loss. Most commonly the materials of interest are metals such as steel. However, other material such as ceramics, polymer coatings, diamond-like carbon, and the like can also be used to produce durable surfaces in modern equipment. The lubricant compositions of this disclosure can provide antiwear properties to such surfaces.

The lubricant compositions of this disclosure are stable without rapidly separating and provide advantaged wear, including advantaged wear performance in the lubrication of internal combustion engines, power trains, drivelines, transmissions, gears, gear trains, gear sets, compressors, pumps, hydraulic systems, bearings, bushings, turbines, and the like.

Also, the lubricant compositions of this disclosure are stable without rapidly separating and provide advantaged wear, including advantaged wear performance in the lubrication of mechanical components, which can include, for example, pistons, piston rings, cylinder liners, cylinders, cams, tappets, lifters, bearings (journal, roller, tapered, needle, ball, and the like), gears, valves, and the like.

Further, the lubricant compositions of this disclosure provide advantaged wear, including advantaged wear and solubility performance as a component in lubricant compositions, which can include, for example, lubricating liquids, semi-solids, solids, greases, dispersions, suspensions, material concentrates, additive concentrates, and the like.

The lubricant compositions of this disclosure are useful in additive concentrates that include the combination of the minor component of this disclosure with at least one other additive component, having combined weight % concentrations in the range of 1% to 80%, preferably 2% to 60%, more preferably 3% to 50%, even more preferably 4% to 40%, and in some instances preferably 5% to 30%.

Yet further, the lubricant compositions of this disclosure are stable without rapidly separating and provide advantaged wear, including advantaged wear performance under diverse lubrication regimes, that include, for example, hydrodynamic, elastohydrodynamic, boundary, mixed lubrication, extreme pressure regimes, and the like.

The lubricant compositions of this disclosure are stable without rapidly separating and provide advantaged wear, including advantaged wear performance under a range of lubrication contact pressures, from 1 MPas to greater than 10 GPas, preferably greater than 10 MPas, more preferably greater that 100 MPas, even more preferably greater than 300 MPas. Under certain circumstances, the lubricant compositions of this disclosure provide advantaged wear, including advantaged wear and solubility, performance at greater than 0.5 GPas, often at greater than 1 GPas, sometimes greater than 2 GPas, under selected circumstances greater than 5 GPas.

Also, the lubricant compositions of this disclosure are stable without rapidly separating and provide advantaged wear, including advantaged wear performance in spark-ignition internal combustion engines, compression-ignition internal combustion engines, mixed-ignition (spark-assisted and compression) internal combustion engines, jet- or plasma-ignition internal combustion engines, and the like.

Further, the lubricant compositions of this disclosure are stable without rapidly separating and provide advantaged wear, including advantaged wear performance in diverse engine types, which can include, for example, the following: 2-stroke engines; 4-stroke engine; engines with alternate stroke designs greater than 2-stroke, such as 5-stroke, or 7-stroke, and the like; rotary engines; dedicated EGR (exhaust gas recirculation) fueled engines; free-piston engine; engines that function in hybrid propulsion systems, that can further include electrical-based power systems, hydraulic-based power systems, diverse system designs such as parallel, series, non-parallel, and the like.

Yet further, the lubricant compositions of this disclosure are stable without rapidly separating and provide advantaged wear, including advantaged wear performance in, for example, the following: naturally aspirated engines; turbocharged and supercharged, port-fueled injection engines; turbocharged and supercharged, direct injection engines (for gasoline, diesel, natural gas, and other fuel types); turbocharged engines designed to operate with in-cylinder combustion pressures of greater than 12 bar, preferably greater than 18 bar, more preferably greater than 20 bar, even more preferably greater than 22 bar, and in certain instances combustion pressures greater than 24 bar, even greater than 26 bar, and even more so greater than 28 bar, and with particular designs greater than 30 bar; engines having low-temperature burn combustion, lean-burn combustion, and high thermal efficiency designs.

Also, the lubricant compositions of this disclosure are stable without rapidly separating and provide advantaged wear, including advantaged wear performance in engines that are fueled with fuel compositions that include, for example, the following: gasoline; distillate fuel, diesel fuel, jet fuel, gas-to-liquid and Fischer-Tropsch-derived high-cetane fuels; compressed natural gas, liquefied natural gas, methane, ethane, propane, other natural gas components, other natural gas liquids; ethanol, methanol, other higher MW alcohols; FAMEs, vegetable-derived esters and polyesters; biodiesel, bio-derived and bio-based fuels; hydrogen; dimethyl ether; other alternate fuels; fuels diluted with EGR (exhaust gas recirculation) gases, with EGR gases enriched in hydrogen or carbon monoxide or combinations of $H_2$/CO, in both dilute and high concentration (in concentrations of >0.1%, preferably >0.5%, more preferably >1%, even more preferably >2%, and even more so preferably >3%), and blends or combinations of these in proportions that enhance combustion efficiency, power, cleanliness, anti-knock, and anti-LSPI (low speed pre-ignition).

Further, the lubricant compositions of this disclosure are stable without rapidly separating and provide advantaged wear, including advantaged wear performance on lubricated surfaces that include, for example, the following: metals, metal alloys, non-metals, non-metal alloys, mixed carbon-metal composites and alloys, mixed carbon-nonmetal composites and alloys, ferrous metals, ferrous composites and alloys, non-ferrous metals, non-ferrous composites and alloys, titanium, titanium composites and alloys, aluminum, aluminum composites and alloys, magnesium, magnesium composites and alloys, ion-implanted metals and alloys, plasma modified surfaces; surface modified materials; coatings; mono-layer, multi-layer, and gradient layered coatings; honed surfaces; polished surfaces; etched surfaces; textured surfaces; micro and nano structures on textured surfaces; super-finished surfaces; diamond-like carbon (DLC), DLC with high-hydrogen content, DLC with moderate hydrogen content, DLC with low-hydrogen content, DLC with near-zero hydrogen content, DLC composites, DLC-metal compositions and composites, DLC-nonmetal compositions and composites; ceramics, ceramic oxides, ceramic nitrides, FeN, CrN, ceramic carbides, mixed ceramic compositions, and the like; polymers, thermoplastic polymers, engineered polymers, polymer blends, polymer alloys, polymer composites; materials compositions and composites containing dry lubricants, that include, for example, graphite, carbon, molybdenum, molybdenum disulfide, polytetrafluoroethylene, polyperfluoropropylene, polyperfluoroalkylethers, and the like.

Yet further, the lubricant compositions of this disclosure are stable without rapidly separating and provide advantaged wear, including advantaged wear performance on lubricated surfaces of 3-D printed materials, with or without post-printing surface finishing; surfaces of 3-D printed materials that have been post-printing treated with coatings, which may include plasma spray coatings, ion beam-generated coatings, electrolytically- or galvanically-generated coatings, electro-deposition coatings, vapor-deposition coatings, liquid-deposition coatings, thermal coatings, laser-based coatings; surfaces of 3-D printed materials, where the surfaces may be as-printed, finished, or coated, that include: metals, metal alloys, non-metals, non-metal alloys, mixed carbon-metal composites and alloys, mixed carbon-nonmetal composites and alloys, ferrous metals, ferrous composites and alloys, non-ferrous metals, non-ferrous composites and alloys, titanium, titanium composites and alloys, aluminum, aluminum composites and alloys, magnesium, magnesium composites and alloys, ion-implanted metals and alloys; plasma modified surfaces; surface modified materials; mono-layer, multi-layer, and gradient layered coatings; honed surfaces; polished surfaces; etched surfaces; textured surfaces; micro and nano structures on textured surfaces; super-finished surfaces; diamond-like carbon (DLC), DLC with high-hydrogen content, DLC with moderate hydrogen content, DLC with low-hydrogen content, DLC with near-zero hydrogen content, DLC composites, DLC-metal compositions and composites, DLC-nonmetal compositions and composites; ceramics, ceramic oxides, ceramic nitrides, FeN, CrN, ceramic carbides, mixed ceramic compositions, and the like; polymers, thermoplastic polymers, engineered polymers, polymer blends, polymer alloys, polymer composites; materials compositions and composites containing dry lubricants, that include, for example, graphite, carbon, molybdenum, molybdenum disulfide, polytetrafluoroethylene, polyperfluoropropylene, polyperfluoroalkylethers, and the like.

Still further, the lubricant compositions of this disclosure provide advantaged synergistic wear, including advantaged synergistic wear and solubility, performance in combination with one or more performance additives, with performance additives at effective concentration ranges, and with performance additives at effective ratios with the minor component of this disclosure.

Lubricating Oil Base Stocks

A wide range of lubricating base oils is known in the art. Lubricating base oils that are useful in the present disclosure are natural oils, mineral oils and synthetic oils, and unconventional oils (or mixtures thereof) can be used unrefined, refined, or rerefined (the latter is also known as reclaimed or reprocessed oil). Unrefined oils are those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve at least one lubricating oil property. One skilled in the art is familiar with many purification processes. These processes include solvent extraction, secondary distillation, acid extraction, base extraction, filtration, and percolation. Rerefined oils are obtained by processes analogous to refined oils but using an oil that has been previously used as a feed stock.

Groups I, II, III, IV and V are broad base oil stock categories developed and defined by the American Petroleum Institute (API Publication 1509; www.API.org) to create guidelines for lubricant base oils. Group I base stocks have a viscosity index of between about 80 to 120 and contain greater than about 0.03% sulfur and/or less than about 90% saturates. Group II base stocks have a viscosity index of between about 80 to 120, and contain less than or equal to about 0.03% sulfur and greater than or equal to about 90% saturates. Group III stocks have a viscosity index greater than about 120 and contain less than or equal to about 0.03% sulfur and greater than about 90% saturates. Group IV includes polyalphaolefins (PAO). Group V base stock includes base stocks not included in Groups I-IV. The table below summarizes properties of each of these five groups.

| Base Oil Properties | | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | polyalphaolefins (PAO) | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale are also useful. Natural oils vary also as to the method used for their production and purification, for example, their distillation range and whether they are straight run or cracked, hydrorefined, or solvent extracted.

Group II and/or Group III hydroprocessed or hydrocracked base stocks, including synthetic oils such as alkyl aromatics and synthetic esters are also well known base stock oils.

Synthetic oils include hydrocarbon oil. Hydrocarbon oils include oils such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks are commonly used synthetic hydrocarbon oil. By way of example, PAOs derived from $C_8$, $C_{10}$, $C_{12}$, $C_{14}$ olefins or mixtures thereof may be utilized. See U.S. Pat. Nos. 4,956,122; 4,827,064; and 4,827,073.

The number average molecular weights of the PAOs, which are known materials and generally available on a major commercial scale from suppliers such as ExxonMobil Chemical Company, Chevron Phillips Chemical Company, BP, and others, typically vary from about 250 to about 3,000, although PAO's may be made in viscosities up to about 150 cSt (100° C.). The PAOs are typically comprised of relatively low molecular weight hydrogenated polymers or oligomers of alphaolefins which include, but are not limited to, $C_2$ to about $C_{32}$ alphaolefins with the $C_8$ to about $C_{16}$ alphaolefins, such as 1-octene, 1-decene, 1-dodecene and the like, being preferred. The preferred polyalphaolefins are poly-1-octene, poly-1-decene and poly-1-dodecene and mixtures thereof and mixed olefin-derived polyolefins. However, the dimers of higher olefins in the range of $C_{14}$ to $C_{18}$ may be used to provide low viscosity base stocks of acceptably low volatility. Depending on the viscosity grade and the starting oligomer, the PAOs may be predominantly trimers and tetramers of the starting olefins, with minor amounts of the higher oligomers, having a viscosity range of 1.5 to 12 cSt. PAO fluids of particular use may include 3.0 cSt, 3.4 cSt, and/or 3.6 cSt and combinations thereof. Mixtures of PAO fluids having a viscosity range of 1.5 to approximately 150 cSt or more may be used if desired.

The PAO fluids may be conveniently made by the polymerization of an alphaolefin in the presence of a polymerization catalyst such as the Friedel-Crafts catalysts including, for example, aluminum trichloride, boron trifluoride or complexes of boron trifluoride with water, alcohols such as ethanol, propanol or butanol, carboxylic acids or esters such as ethyl acetate or ethyl propionate. For example the methods disclosed by U.S. Pat. Nos. 4,149,178 or 3,382,291 may be conveniently used herein. Other descriptions of PAO synthesis are found in the following U.S. Pat. Nos. 3,742,082; 3,769,363; 3,876,720; 4,239,930; 4,367,352; 4,413,156; 4,434,408; 4,910,355; 4,956,122; and 5,068,487. The dimers of the $C_{14}$ to $C_{18}$ olefins are described in U.S. Pat. No. 4,218,330.

Other useful lubricant oil base stocks include wax isomerate base stocks and base oils, comprising hydroisomerized waxy stocks (e.g. waxy stocks such as gas oils, slack waxes, fuels hydrocracker bottoms, etc.), hydroisomerized Fischer-Tropsch waxes, Gas-to-Liquids (GTL) base stocks and base oils, and other wax isomerate hydroisomerized base stocks and base oils, or mixtures thereof. Fischer-Tropsch waxes, the high boiling point residues of Fischer-Tropsch synthesis, are highly paraffinic hydrocarbons with very low sulfur content. The hydroprocessing used for the production of such base stocks may use an amorphous hydrocracking/hydroisomerization catalyst, such as one of the specialized lube hydrocracking (LHDC) catalysts or a crystalline hydrocracking/hydroisomerization catalyst, preferably a zeolitic catalyst. For example, one useful catalyst is ZSM-48 as described in U.S. Pat. No. 5,075,269, the disclosure of which is incorporated herein by reference in its entirety. Processes for making hydrocracked/hydroisomerized distillates and hydrocracked/hydroisomerized waxes are described, for example, in U.S. Pat. Nos. 2,817,693; 4,975,177; 4,921,594 and 4,897,178 as well as in British Patent Nos. 1,429,494; 1,350,257; 1,440,230 and 1,390,359. Each of the aforementioned patents is incorporated herein in their entirety. Particularly favorable processes are described in European Patent Application Nos. 464546 and 464547, also incorporated herein by reference. Processes using Fischer-Tropsch wax feeds are described in U.S. Pat. Nos. 4,594,172 and 4,943,672, the disclosures of which are incorporated herein by reference in their entirety.

Gas-to-Liquids (GTL) base oils, Fischer-Tropsch wax derived base oils, and other wax-derived hydroisomerized (wax isomerate) base oils be advantageously used in the instant disclosure, and may have useful kinematic viscosities at 100° C. of about 3 cSt to about 50 cSt, preferably about 3 cSt to about 30 cSt, more preferably about 3.5 cSt to about 25 cSt, as exemplified by GTL 4 with kinematic viscosity of about 4.0 cSt at 100° C. and a viscosity index of about 141. These Gas-to-Liquids (GTL) base oils, Fischer-Tropsch wax derived base oils, and other wax-derived hydroisomerized base oils may have useful pour points of about −20° C. or lower, and under some conditions may have advantageous pour points of about −25° C. or lower, with useful pour points of about −30° C. to about −40° C. or lower. Useful compositions of Gas-to-Liquids (GTL) base oils, Fischer-Tropsch wax derived base oils, and wax-derived hydroisomerized base oils are recited in U.S. Pat. Nos. 6,080,301; 6,090,989, and 6,165,949 for example, and are incorporated herein in their entirety by reference.

The hydrocarbyl aromatics can be used as a base oil or base oil component and can be any hydrocarbyl molecule that contains at least about 5% of its weight derived from an aromatic moiety such as a benzenoid moiety or naphthenoid moiety, or their derivatives. These hydrocarbyl aromatics include alkyl benzenes, alkyl naphthalenes, alkyl diphenyl oxides, alkyl naphthols, alkyl diphenyl sulfides, alkylated bis-phenol A, alkylated thiodiphenol, and the like. The aromatic can be mono-alkylated, dialkylated, polyalkylated, and the like. The aromatic can be mono- or poly-functionalized. The hydrocarbyl groups can also be comprised of mixtures of alkyl groups, alkenyl groups, alkynyl, cycloalkyl groups, cycloalkenyl groups and other related hydrocarbyl groups. The hydrocarbyl groups can range from about $C_6$ up to about $C_{60}$ with a range of about $C_8$ to about $C_{20}$ often being preferred. A mixture of hydrocarbyl groups is often preferred, and up to about three such substituents may be present. The hydrocarbyl group can optionally contain sulfur, oxygen, and/or nitrogen containing substituents. The aromatic group can also be derived from natural (petroleum) sources, provided at least about 5% of the molecule is comprised of an above-type aromatic moiety. Viscosities at 100° C. of approximately 3 cSt to about 50 cSt are preferred, with viscosities of approximately 3.4 cSt to about 20 cSt often being more preferred for the hydrocarbyl aromatic component. In one embodiment, an alkyl naphthalene where the alkyl group is primarily comprised of 1-hexadecene is used. Other alkylates of aromatics can be advantageously used. Naphthalene or methyl naphthalene, for example, can be alkylated with olefins such as octene, decene, dodecene, tetradecene or higher, mixtures of similar olefins, and the like. Useful concentrations of hydrocarbyl aromatic in a lubricant oil composition can be about 2% to about 25%, preferably about 4% to about 20%, and more preferably about 4% to about 15%, depending on the application.

Alkylated aromatics such as the hydrocarbyl aromatics of the present disclosure may be produced by well-known Friedel-Crafts alkylation of aromatic compounds. See Friedel-Crafts and Related Reactions, Olah, G. A. (ed.), Inter-science Publishers, New York, 1963. For example, an aromatic compound, such as benzene or naphthalene, is alkylated by an olefin, alkyl halide or alcohol in the presence of a Friedel-Crafts catalyst. See Friedel-Crafts and Related Reactions, Vol. 2, part 1, chapters 14, 17, and 18, See Olah, G. A. (ed.), Inter-science Publishers, New York, 1964. Many homogeneous or heterogeneous, solid catalysts are known to one skilled in the art. The choice of catalyst depends on the reactivity of the starting materials and product quality requirements. For example, strong acids such as $AlCl_3$, $BF_3$, or HF may be used. In some cases, milder catalysts such as $FeCl_3$ or $SnCl_4$ are preferred. Newer alkylation technology uses zeolites or solid super acids.

Esters comprise a useful base stock. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid, etc., with a variety of alcohols such as butyl alcohol, hexyl alcohol, dodecyl alcohol, 2-ethylhexyl alcohol, etc. Specific examples of these types of esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, etc.

Particularly useful synthetic esters are those which are obtained by reacting one or more polyhydric alcohols, preferably the hindered polyols (such as the neopentyl polyols, e.g., neopentyl glycol, trimethylol ethane, 2-methyl-2-propyl-1,3-propanediol, trimethylol propane, pentaerythritol and dipentaerythritol) with alkanoic acids containing at least about 4 carbon atoms, preferably $C_5$ to $C_{30}$ acids such as saturated straight chain fatty acids including caprylic acid, capric acid, lauric acid, myristic acid, palmitic acid, stearic acid, arachic acid, and behenic acid, or the corresponding branched chain fatty acids or unsaturated fatty acids such as oleic acid, or mixtures of any of these materials.

Suitable synthetic ester components include the esters of trimethylol propane, trimethylol butane, trimethylol ethane, pentaerythritol and/or dipentaerythritol with one or more monocarboxylic acids containing from about 5 to about 10 carbon atoms. These esters are widely available commercially, for example, the Mobil P-41 and P-51 esters of ExxonMobil Chemical Company.

Also useful are esters derived from renewable material such as coconut, palm, rapeseed, soy, sunflower and the like. These esters may be monoesters, di-esters, polyol esters, complex esters, or mixtures thereof. These esters are widely available commercially, for example, the Mobil P-51 ester of ExxonMobil Chemical Company.

Engine oil formulations containing renewable esters are included in this disclosure. For such formulations, the renewable content of the ester is typically greater than about 70 weight percent, preferably more than about 80 weight percent and most preferably more than about 90 weight percent.

Other useful fluids of lubricating viscosity include non-conventional or unconventional base stocks that have been processed, preferably catalytically, or synthesized to provide high performance lubrication characteristics.

Non-conventional or unconventional base stocks/base oils include one or more of a mixture of base stock(s) derived from one or more Gas-to-Liquids (GTL) materials, as well as isomerate/isodewaxate base stock(s) derived from natural wax or waxy feeds, mineral and or non-mineral oil waxy feed stocks such as slack waxes, natural waxes, and waxy stocks such as gas oils, waxy fuels hydrocracker bottoms, waxy raffinate, hydrocrackate, thermal crackates, or other mineral, mineral oil, or even non-petroleum oil derived waxy materials such as waxy materials received from coal liquefaction or shale oil, and mixtures of such base stocks.

GTL materials are materials that are derived via one or more synthesis, combination, transformation, rearrangement, and/or degradation/deconstructive processes from gaseous carbon-containing compounds, hydrogen-containing compounds and/or elements as feed stocks such as hydrogen, carbon dioxide, carbon monoxide, water, methane, ethane, ethylene, acetylene, propane, propylene, propyne, butane, butylenes, and butynes. GTL base stocks and/or base oils are GTL materials of lubricating viscosity that are generally derived from hydrocarbons; for example, waxy synthesized hydrocarbons, that are themselves derived from simpler gaseous carbon-containing compounds, hydrogen-containing compounds and/or elements as feed stocks. GTL base stock(s) and/or base oil(s) include oils boiling in the lube oil boiling range (1) separated/fractionated from synthesized GTL materials such as, for example, by distillation and subsequently subjected to a final wax processing step which involves either or both of a catalytic dewaxing process, or a solvent dewaxing process, to produce lube oils of reduced/low pour point; (2) synthesized wax isomerates, comprising, for example, hydrodewaxed or hydroisomerized cat and/or solvent dewaxed synthesized wax or waxy hydrocarbons; (3) hydrodewaxed or hydroisomerized cat and/or solvent dewaxed Fischer-Tropsch (F-T) material (i.e., hydrocarbons, waxy hydrocarbons, waxes and possible analogous oxygenates); preferably hydrodewaxed or hydroisomerized/followed by cat and/or solvent dewaxing dewaxed F-T waxy hydrocarbons, or hydrodewaxed or hydroisomerized/followed by cat (or solvent) dewaxing dewaxed, F-T waxes, or mixtures thereof.

GTL base stock(s) and/or base oil(s) derived from GTL materials, especially, hydrodewaxed or hydroisomerized/ followed by cat and/or solvent dewaxed wax or waxy feed, preferably F-T material derived base stock(s) and/or base oil(s), are characterized typically as having kinematic viscosities at 100° C. of from about 2 mm²/s to about 50 mm²/s (ASTM D445). They are further characterized typically as having pour points of −5° C. to about −40° C. or lower (ASTM D97). They are also characterized typically as having viscosity indices of about 80 to about 140 or greater (ASTM D2270).

In addition, the GTL base stock(s) and/or base oil(s) are typically highly paraffinic (>90% saturates), and may contain mixtures of monocycloparaffins and multicycloparaffins in combination with non-cyclic isoparaffins. The ratio of the naphthenic (i.e., cycloparaffin) content in such combinations varies with the catalyst and temperature used. Further, GTL base stock(s) and/or base oil(s) typically have very low sulfur and nitrogen content, generally containing less than about 10 ppm, and more typically less than about 5 ppm of each of these elements. The sulfur and nitrogen content of GTL base stock(s) and/or base oil(s) obtained from F-T material, especially F-T wax, is essentially nil. In addition, the absence of phosphorous and aromatics make this materially especially suitable for the formulation of low SAP products.

The term GTL base stock and/or base oil and/or wax isomerate base stock and/or base oil is to be understood as embracing individual fractions of such materials of wide viscosity range as recovered in the production process, mixtures of two or more of such fractions, as well as mixtures of one or two or more low viscosity fractions with one, two or more higher viscosity fractions to produce a blend wherein the blend exhibits a target kinematic viscosity.

The GTL material, from which the GTL base stock(s) and/or base oil(s) is/are derived is preferably an F-T material (i.e., hydrocarbons, waxy hydrocarbons, wax).

Base oils for use in the formulated lubricating oils useful in the present disclosure are any of the variety of oils corresponding to API Group I, Group II, Group III, Group IV, and Group V oils and mixtures thereof, preferably API Group II, Group III, Group IV, and Group V oils and mixtures thereof, more preferably the Group III to Group V base oils due to their exceptional volatility, stability, viscometric and cleanliness features. Minor quantities of Group I stock, such as the amount used to dilute additives for blending into formulated lube oil products, can be tolerated but should be kept to a minimum, i.e. amounts only associated with their use as diluent/carrier oil for additives used on an "as-received" basis. Even in regard to the Group II stocks, it is preferred that the Group II stock be in the higher quality range associated with that stock, i.e. a Group II stock having a viscosity index in the range 100<VI<120.

The base oil constitutes the major component of the engine or other mechanical component oil lubricant composition of the present disclosure and typically is present in an amount ranging from about 50 to about 99 weight percent, preferably from about 70 to about 95 weight percent, and more preferably from about 85 to about 95 weight percent, based on the total weight of the composition. The base oil may be selected from any of the synthetic or natural oils typically used as crankcase lubricating oils for spark-ignited and compression-ignited engines. The base oil conveniently has a kinematic viscosity, according to ASTM standards, of about 2.5 cSt to about 12 cSt (or mm²/s) at 100° C. and preferably of about 2.5 cSt to about 9 cSt (or mm²/s) at 100° C. Mixtures of synthetic and natural base oils may be used if desired. Bi-modal mixtures of Group I, II, III, IV, and/or V base stocks may be used if desired.

Antiwear Additive

An illustrative antiwear additive useful in this disclosure includes, for example, a phosphazene represented by the formula

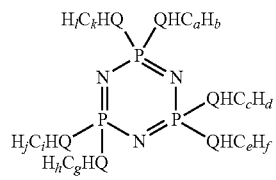

wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. Preferably, a, c, e, g, i and k are a value of 3 (propyl) or 4 (butyl) wherein the ratio of propyl to butyl groups is between about 1:10 and about 10:1, more preferably between about 1:3 and about 3:1. The substituents can be saturated or unsaturated.

Illustrative phosphazenes are represented by the formulae

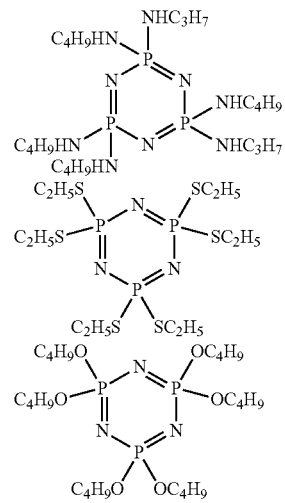

A preferred phosphazene is represented by the formula

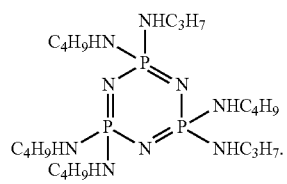

When the phosphazene represented by the above formula (e.g., (propylamino-co-butylamino)cyclotriphosphazene) is used as an additive in an engine or other mechanical component lubricating oil, wear control is improved as compared to wear control achieved using a lubricating oil containing an antiwear additive other than the phosphazene.

Further, when the phosphazene represented by the above formula (e.g., (propylamino-co-butylamino)cyclotriphosphazene) is used as an additive in an engine or other mechanical component lubricating oil, wear control is improved as compared to wear control achieved using a lubricating oil containing an antiwear additive other than the phosphazene.

It has been surprisingly found that phosphazenes with mixed substituent groups (e.g., a mixture of propyl and butyl groups) substituted on the phosphorus have improved solubility in hydrocarbon basestocks (e.g., PAO), and form stable lubricant blends without rapidly dropping out.

An illustrative process for preparing phosphazenes represented by the above formulae involves reacting one or more alkylamines, thiols or alcohols, and one or more phosphazene precursors in the presence of a solvent and under reaction conditions sufficient to prepare the phosphazenes represented by the above formula. The process also involves washing the reaction mixture in one or more solvents (e.g., water), and drying the reaction mixture.

A preferred process of this disclosure involves preparing a composition represented by the formula

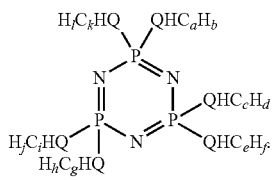

wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value. The process involves reacting one or more alkylamines, thiols or alcohols and one or more phosphazene precursors in the presence of a solvent and under reaction conditions sufficient to prepare the phosphazenes represented by the above formula. The process also involves washing the reaction mixture in one or more solvents (e.g., water), and drying the reaction mixture.

Illustrative alkylamine reactants useful in the process of this disclosure include, for example, ethyl amine, propyl amine, butyl amine, pentyl amine, hexyl amine, ethylene amine, propylene amine, butylene amine, pentylene amine, hexylene amine, and the like. Illustrative alkylthiol reactants useful in the process of this disclosure include, for example, ethanethiol, propanethiol, butanethiol, pentanethiol, hexanethiol, and the like. Illustrative alcohol reactants useful in the process of this disclosure include, for example, ethanol, propanol, butanol, pentanol hexanol and the like. Alkyl groups may be straight or branched. Alkyl groups may also include double bonds. Illustrative phosphazene precursor reactants useful in the process of this disclosure include, for example, hexachlorocyclotriphosphazene, and the like. Illustrative reaction solvents useful in the process of this disclosure include, for example, hydrocarbon solvents such as THF or mineral oil, chlorinated solvents such as dichloromethane or tricholoro ethane, and the like.

Reaction conditions for the reaction of the alkylamine and phosphazene precursor, such as temperature, pressure and contact time, may also vary greatly and any suitable combination of such conditions may be employed herein. The reaction temperature may range between about −10° C. to about 250° C., and preferably between about 0° C. to about 200° C., and more preferably between about 25° C. to about 150° C. Normally the reaction is carried out under ambient pressure and the contact time may vary from a matter of seconds or minutes to a few hours or greater. The reactants can be added to the reaction mixture or combined in any order. The stir time employed can range from about 0.5 to about 72 hours, preferably from about 1 to 36 hours, and more preferably from about 2 to 24 hours.

Examples of techniques that can be employed to characterize the compositions formed by the process described above include, but are not limited to, analytical gas chromatography, FTIR spectroscopy, nuclear magnetic resonance, thermogravimetric analysis (TGA), inductively coupled plasma mass spectrometry, differential scanning calorimetry (DSC), volatility and viscosity measurements.

The phosphazene represented by the above formula is present in the engine or other mechanical component oil formulations of this disclosure in low concentrations. In particular, the phosphazene represented by the above formula is present in the engine or other mechanical component oil formulations of this disclosure in an amount of from about 0.01 weight percent to about 5 weight percent, preferably from about 0.1 to about 2 weight percent, and more preferably from about 0.5 to about 1.5 weight percent, based on the total weight of the formulated oil. Wear control is improved and solubility maintained in an engine or other mechanical component lubricated with a lubricating oil by including a phosphazene additive of this disclosure in low concentration in the lubricating oil.

Other Additives

The formulated lubricating oil useful in the present disclosure may additionally contain one or more of the other commonly used lubricating oil performance additives including but not limited to other antiwear additives, detergents, dispersants, viscosity modifiers, corrosion inhibitors, rust inhibitors, metal deactivators, extreme pressure additives, anti-seizure agents, wax modifiers, other viscosity modifiers, fluid-loss additives, seal compatibility agents, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, Fla.; ISBN 0-89573-177-0. Reference is also made to "Lubricant Additives" by M. W. Ranney, published by Noyes Data Corporation of Parkridge, N.J. (1973); see also U.S. Pat. No. 7,704,930, the disclosure of which is incorporated herein in its entirety. These additives are commonly delivered with varying amounts of diluent oil, that may range from 5 weight percent to 50 weight percent.

The additives useful in this disclosure do not have to be soluble in the lubricating oils. Insoluble additives such as zinc stearate in oil can be dispersed in the lubricating oils of this disclosure.

The types and quantities of performance additives used in combination with the instant disclosure in lubricant compositions are not limited by the examples shown herein as illustrations.

Other Antiwear Additives

Illustrative antiwear additives useful in this disclosure include, for example, metal salts of a carboxylic acid. The metal is selected from a transition metal and mixtures thereof. The carboxylic acid is selected from an aliphatic carboxylic acid, a cycloaliphatic carboxylic acid, an aromatic carboxylic acid, and mixtures thereof.

The metal is preferably selected from a Group 10, 11 and 12 metal, and mixtures thereof. The carboxylic acid is preferably an aliphatic, saturated, unbranched carboxylic acid having from about 8 to about 26 carbon atoms, and mixtures thereof.

The metal is preferably selected from nickel (Ni), palladium (Pd), platinum (Pt), copper (Cu), silver (Ag), gold (Au), zinc (Zn), and mixtures thereof.

The carboxylic acid is preferably selected from caprylic acid (C8), pelargonic acid (C9), capric acid (C10), undecylic acid (C11), lauric acid (C12), tridecylic acid (C13), myristic acid (C14), pentadecylic acid (C15), palmitic acid (C16), margaric acid (C17), isostearic acid (C18), stearic acid (C18), nonadecylic acid (C19), arachidic acid (C20), heneicosylic acid (C21), behenic acid (C22), tricosylic acid (C23), lignoceric acid (C24), pentacosylic acid (C25), cerotic acid (C26), and mixtures thereof.

Preferably, the metal salt of a carboxylic acid comprises zinc stearate, silver stearate, palladium stearate, zinc palmitate, silver palmitate, palladium palmitate, and mixtures thereof.

The metal salt of a carboxylic acid is present in the engine or other mechanical component oil formulations of this disclosure in an amount of from about 0.01 weight percent to about 5 weight percent, based on the total weight of the formulated oil.

Low phosphorus engine or other mechanical component oil formulations are included in this disclosure. For such formulations, the phosphorus content is typically less than about 0.12 weight percent, preferably less than about 0.10 weight percent, more preferably less than about 0.085 weight percent, and most preferably less than about 0.04 weight percent.

A metal alkylthiophosphate and more particularly a metal dialkyl dithio phosphate in which the metal constituent is zinc, or zinc dialkyl dithio phosphate (ZDDP) can be a useful component of the lubricating oils of this disclosure. ZDDP can be derived from primary alcohols, secondary alcohols or mixtures thereof. ZDDP compounds generally are of the formula

$$Zn[SP(S)(OR^1)(OR^2)]_2$$

where $R^1$ and $R^2$ are $C_1$-$C_{18}$ alkyl groups, preferably $C_2$-$C_{12}$ alkyl groups. These alkyl groups may be straight chain or branched. Alcohols used in the ZDDP can be 2-propanol, butanol, secondary butanol, pentanols, hexanols such as 4-methyl-2-pentanol, n-hexanol, n-octanol, 2-ethyl hexanol, alkylated phenols, and the like. Mixtures of secondary alcohols or of primary and secondary alcohol can be preferred. Alkyl aryl groups may also be used.

Preferable zinc dithiophosphates which are commercially available include secondary zinc dithiophosphates such as those available from for example, The Lubrizol Corporation under the trade designations "LZ 677A", "LZ 1095" and "LZ 1371", from for example Chevron Oronite under the trade designation "OLOA 262" and from for example Afton Chemical under the trade designation "HITEC 7169".

The ZDDP is typically used in amounts of from about 0.4 weight percent to about 1.2 weight percent, preferably from about 0.5 weight percent to about 1.0 weight percent, and more preferably from about 0.6 weight percent to about 0.8 weight percent, based on the total weight of the lubricating oil, although more or less can often be used advantageously. Preferably, the ZDDP is a secondary ZDDP and present in an amount of from about 0.6 to 1.0 weight percent of the total weight of the lubricating oil.

Low phosphorus engine or other mechanical component oil formulations are included in this disclosure. For such formulations, the phosphorus content is typically less than about 0.12 weight percent preferably less than about 0.10 weight percent and most preferably less than about 0.085 weight percent.

Detergents

Illustrative detergents useful in this disclosure include, for example, alkali metal detergents, alkaline earth metal detergents, or mixtures of one or more alkali metal detergents and one or more alkaline earth metal detergents. A typical detergent is an anionic material that contains a long chain hydrophobic portion of the molecule and a smaller anionic or oleophobic hydrophilic portion of the molecule. The anionic portion of the detergent is typically derived from an organic acid such as a sulfur acid, carboxylic acid (e.g., salicylic acid), phosphorous acid, phenol, or mixtures thereof. The counterion is typically an alkaline earth or alkali metal. The detergent can be overbased as described herein.

The detergent is preferably a metal salt of an organic or inorganic acid, a metal salt of a phenol, or mixtures thereof. The metal is preferably selected from an alkali metal, an alkaline earth metal, and mixtures thereof. The organic or inorganic acid is selected from an aliphatic organic or inorganic acid, a cycloaliphatic organic or inorganic acid, an aromatic organic or inorganic acid, and mixtures thereof.

The metal is preferably selected from an alkali metal, an alkaline earth metal, and mixtures thereof. More preferably, the metal is selected from calcium (Ca), magnesium (Mg), and mixtures thereof.

The organic acid or inorganic acid is preferably selected from a sulfur acid, a carboxylic acid, a phosphorus acid, and mixtures thereof.

Preferably, the metal salt of an organic or inorganic acid or the metal salt of a phenol comprises calcium phenate, calcium sulfonate, calcium salicylate, magnesium phenate, magnesium sulfonate, magnesium salicylate, an overbased detergent, and mixtures thereof.

Salts that contain a substantially stochiometric amount of the metal are described as neutral salts and have a total base number (TBN, as measured by ASTM D2896) of from 0 to 80. Many compositions are overbased, containing large amounts of a metal base that is achieved by reacting an excess of a metal compound (a metal hydroxide or oxide, for example) with an acidic gas (such as carbon dioxide). Useful detergents can be neutral, mildly overbased, or highly overbased. These detergents can be used in mixtures of neutral, overbased, highly overbased calcium salicylate, sulfonates, phenates and/or magnesium salicylate, sulfonates, phenates. The TBN ranges can vary from low, medium to high TBN products, including as low as 0 to as high as 600. Preferably the TBN delivered by the detergent is between 1 and 20. More preferably between 1 and 12. Mixtures of low, medium, high TBN can be used, along with mixtures of calcium and magnesium metal based detergents, and including sulfonates, phenates, salicylates, and carboxylates. A detergent mixture with a metal ratio of 1, in conjunction of a detergent with a metal ratio of 2, and as high as a detergent with a metal ratio of 5, can be used. Borated detergents can also be used.

Alkaline earth phenates are another useful class of detergent. These detergents can be made by reacting alkaline earth metal hydroxide or oxide (CaO, Ca(OH)$_2$, BaO, Ba(OH)$_2$, MgO, Mg(OH)$_2$, for example) with an alkyl phenol or sulfurized alkylphenol. Useful alkyl groups include straight chain or branched $C_1$-$C_{30}$ alkyl groups, preferably, $C_4$-$C_{20}$ or mixtures thereof. Examples of suitable phenols include isobutylphenol, 2-ethylhexylphenol, nonylphenol, dodecyl phenol, and the like. It should be noted that starting alkylphenols may contain more than one alkyl substituent that are each independently straight chain or branched and can be used from 0.5 to 6 weight percent. When a non-sulfurized alkylphenol is used, the sulfurized product may be obtained by methods well known in the art. These methods include heating a mixture of alkylphenol and sulfurizing agent (including elemental sulfur, sulfur halides such as sulfur dichloride, and the like) and then reacting the sulfurized phenol with an alkaline earth metal base.

In accordance with this disclosure, metal salts of carboxylic acids are preferred detergents. These carboxylic acid detergents may be prepared by reacting a basic metal compound with at least one carboxylic acid and removing free water from the reaction product. These compounds may be overbased to produce the desired TBN level. Detergents made from salicylic acid are one preferred class of detergents derived from carboxylic acids. Useful salicylates include long chain alkyl salicylates. One useful family of compositions is of the formula

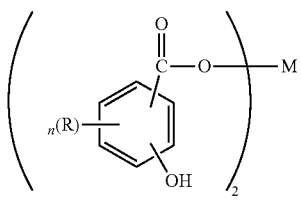

where R is an alkyl group having 1 to about 30 carbon atoms, n is an integer from 1 to 4, and M is an alkaline earth metal. Preferred R groups are alkyl chains of at least $C_{11}$, preferably $C_{13}$ or greater. R may be optionally substituted with substituents that do not interfere with the detergent's function. M is preferably, calcium, magnesium, or barium. More preferably, M is calcium.

Hydrocarbyl-substituted salicylic acids may be prepared from phenols by the Kolbe reaction (see U.S. Pat. No. 3,595,791). The metal salts of the hydrocarbyl-substituted salicylic acids may be prepared by double decomposition of a metal salt in a polar solvent such as water or alcohol.

Alkaline earth metal phosphates are also used as detergents and are known in the art.

Detergents may be simple detergents or what is known as hybrid or complex detergents. The latter detergents can provide the properties of two detergents without the need to blend separate materials. See U.S. Pat. No. 6,034,039.

Preferred detergents include calcium sulfonates, magnesium sulfonates, calcium salicylates, magnesium salicylates, calcium phenates, magnesium phenates, and other related components (including borated detergents), and mixtures thereof. Preferred mixtures of detergents include magnesium sulfonate and calcium salicylate, magnesium sulfonate and calcium sulfonate, magnesium sulfonate and calcium phenate, calcium phenate and calcium salicylate, calcium phenate and calcium sulfonate, calcium phenate and magnesium salicylate, calcium phenate and magnesium phenate. Overbased detergents are also preferred.

The detergent concentration in the lubricating oils of this disclosure can range from about 0.5 to about 6.0 weight percent, preferably about 0.6 to 5.0 weight percent, and more preferably from about 0.8 weight percent to about 4.0 weight percent, based on the total weight of the lubricating oil.

As used herein, the detergent concentrations are given on an "as delivered" basis. Typically, the active detergent is delivered with a process oil. The "as delivered" detergent typically contains from about 20 weight percent to about 100 weight percent, or from about 40 weight percent to about 60 weight percent, of active detergent in the "as delivered" detergent product.

Dispersants

During engine or other mechanical component operation, oil-insoluble oxidation byproducts are produced. Dispersants help keep these byproducts in solution, thus diminishing their deposition on metal surfaces. Dispersants used in the formulation of the lubricating oil may be ashless or ash-forming in nature. Preferably, the dispersant is ashless. So called ashless dispersants are organic materials that form substantially no ash upon combustion. For example, non-metal-containing or borated metal-free dispersants are considered ashless. In contrast, metal-containing detergents discussed above form ash upon combustion.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

A particularly useful class of dispersants are the (poly) alkenylsuccinic derivatives, typically produced by the reaction of a long chain hydrocarbyl substituted succinic compound, usually a hydrocarbyl substituted succinic anhydride, with a polyhydroxy or polyamino compound. The long chain hydrocarbyl group constituting the oleophilic portion of the molecule which confers solubility in the oil, is normally a polyisobutylene group. Many examples of this type of dispersant are well known commercially and in the literature. Exemplary U.S. patents describing such dispersants are U.S. Pat. Nos. 3,172,892; 3,2145,707; 3,219,666; 3,316,177; 3,341,542; 3,444,170; 3,454,607; 3,541,012; 3,630,904; 3,632,511; 3,787,374 and 4,234,435. Other types of dispersant are described in U.S. Pat. Nos. 3,036,003; 3,200,107; 3,254,025; 3,275,554; 3,438,757; 3,454,555; 3,565,804; 3,413,347; 3,697,574; 3,725,277; 3,725,480; 3,726,882; 4,454,059; 3,329,658; 3,449,250; 3,519,565; 3,666,730; 3,687,849; 3,702,300; 4,100,082; 5,705,458. A further description of dispersants may be found, for example, in European Patent Application No. 471 071, to which reference is made for this purpose.

Hydrocarbyl-substituted succinic acid and hydrocarbyl-substituted succinic anhydride derivatives are useful dispersants. In particular, succinimide, succinate esters, or succinate ester amides prepared by the reaction of a hydrocarbon-substituted succinic acid compound preferably having at least 50 carbon atoms in the hydrocarbon substituent, with at least one equivalent of an alkylene amine are particularly useful.

Succinimides are formed by the condensation reaction between hydrocarbyl substituted succinic anhydrides and amines. Molar ratios can vary depending on the polyamine. For example, the molar ratio of hydrocarbyl substituted succinic anhydride to TEPA can vary from about 1:1 to about 5:1. Representative examples are shown in U.S. Pat. Nos.

3,087,936; 3,172,892; 3,219,666; 3,272,746; 3,322,670; and 3,652,616, 3,948,800; and Canada Patent No. 1,094,044.

Succinate esters are formed by the condensation reaction between hydrocarbyl substituted succinic anhydrides and alcohols or polyols. Molar ratios can vary depending on the alcohol or polyol used. For example, the condensation product of a hydrocarbyl substituted succinic anhydride and pentaerythritol is a useful dispersant.

Succinate ester amides are formed by condensation reaction between hydrocarbyl substituted succinic anhydrides and alkanol amines. For example, suitable alkanol amines include ethoxylated polyalkylpolyamines, propoxylated polyalkylpolyamines and polyalkenylpolyamines such as polyethylene polyamines. One example is propoxylated hexamethylenediamine. Representative examples are shown in U.S. Pat. No. 4,426,305.

The molecular weight of the hydrocarbyl substituted succinic anhydrides used in the preceding paragraphs will typically range between 800 and 2,500 or more. The above products can be post-reacted with various reagents such as sulfur, oxygen, formaldehyde, carboxylic acids such as oleic acid. The above products can also be post reacted with boron compounds such as boric acid, borate esters or highly borated dispersants, to form borated dispersants generally having from about 0.1 to about 5 moles of boron per mole of dispersant reaction product.

Mannich base dispersants are made from the reaction of alkylphenols, formaldehyde, and amines. See U.S. Pat. No. 4,767,551, which is incorporated herein by reference. Process aids and catalysts, such as oleic acid and sulfonic acids, can also be part of the reaction mixture. Molecular weights of the alkylphenols range from 800 to 2,500. Representative examples are shown in U.S. Pat. Nos. 3,697,574; 3,703,536; 3,704,308; 3,751,365; 3,756,953; 3,798,165; and 3,803,039.

Typical high molecular weight aliphatic acid modified Mannich condensation products useful in this disclosure can be prepared from high molecular weight alkyl-substituted hydroxyaromatics or $HNR_2$ group-containing reactants.

Hydrocarbyl substituted amine ashless dispersant additives are well known to one skilled in the art; see, for example, U.S. Pat. Nos. 3,275,554; 3,438,757; 3,565,804; 3,755,433, 3,822,209, and 5,084,197.

Preferred dispersants include borated and non-borated succinimides, including those derivatives from mono-succinimides, bis-succinimides, and/or mixtures of mono- and bis-succinimides, wherein the hydrocarbyl succinimide is derived from a hydrocarbylene group such as polyisobutylene having a Mn of from about 500 to about 5000, or from about 1000 to about 3000, or about 1000 to about 2000, or a mixture of such hydrocarbylene groups, often with high terminal vinylic groups. Other preferred dispersants include succinic acid-esters and amides, alkylphenol-polyamine-coupled Mannich adducts, their capped derivatives, and other related components.

Polymethacrylate or polyacrylate derivatives are another class of dispersants. These dispersants are typically prepared by reacting a nitrogen containing monomer and a methacrylic or acrylic acid esters containing 5-25 carbon atoms in the ester group. Representative examples are shown in U.S. Pat. Nos. 2,100,993, and 6,323,164. Polymethacrylate and polyacrylate dispersants are normally used as multifunctional viscosity modifiers. The lower molecular weight versions can be used as lubricant dispersants or fuel detergents.

Illustrative preferred dispersants useful in this disclosure include those derived from polyalkenyl-substituted mono- or dicarboxylic acid, anhydride or ester, which dispersant has a polyalkenyl moiety with a number average molecular weight of at least 900 and from greater than 1.3 to 1.7, preferably from greater than 1.3 to 1.6, most preferably from greater than 1.3 to 1.5, functional groups (mono- or dicarboxylic acid producing moieties) per polyalkenyl moiety (a medium functionality dispersant). Functionality (F) can be determined according to the following formula:

$$F=(SAP \times M_n)/((112,200 \times A.I.)-(SAP \times 98))$$

wherein SAP is the saponification number (i.e., the number of milligrams of KOH consumed in the complete neutralization of the acid groups in one gram of the succinic-containing reaction product, as determined according to ASTM D94); $M_n$ is the number average molecular weight of the starting olefin polymer; and A.I. is the percent active ingredient of the succinic-containing reaction product (the remainder being unreacted olefin polymer, succinic anhydride and diluent).

The polyalkenyl moiety of the dispersant may have a number average molecular weight of at least 900, suitably at least 1500, preferably between 1800 and 3000, such as between 2000 and 2800, more preferably from about 2100 to 2500, and most preferably from about 2200 to about 2400. The molecular weight of a dispersant is generally expressed in terms of the molecular weight of the polyalkenyl moiety. This is because the precise molecular weight range of the dispersant depends on numerous parameters including the type of polymer used to derive the dispersant, the number of functional groups, and the type of nucleophilic group employed.

Polymer molecular weight, specifically $M_n$, can be determined by various known techniques. One convenient method is gel permeation chromatography (GPC), which additionally provides molecular weight distribution information (see W. W. Yau, J. J. Kirkland and D. D. Bly, "Modern Size Exclusion Liquid Chromatography", John Wiley and Sons, New York, 1979). Another useful method for determining molecular weight, particularly for lower molecular weight polymers, is vapor pressure osmometry (e.g., ASTM D3592).

The polyalkenyl moiety in a dispersant preferably has a narrow molecular weight distribution (MWD), also referred to as polydispersity, as determined by the ratio of weight average molecular weight ($M_w$) to number average molecular weight ($M_n$). Polymers having a $M_w/M_n$ of less than 2.2, preferably less than 2.0, are most desirable. Suitable polymers have a polydispersity of from about 1.5 to 2.1, preferably from about 1.6 to about 1.8.

Suitable polyalkenes employed in the formation of the dispersants include homopolymers, interpolymers or lower molecular weight hydrocarbons. One family of such polymers comprise polymers of ethylene and/or at least one $C_3$ to $C_2$ alpha-olefin having the formula $H_2C=CHR^1$ wherein $R^1$ is a straight or branched chain alkyl radical comprising 1 to 26 carbon atoms and wherein the polymer contains carbon-to-carbon unsaturation, and a high degree of terminal ethenylidene unsaturation. Preferably, such polymers comprise interpolymers of ethylene and at least one alpha-olefin of the above formula, wherein $R^1$ is alkyl of from 1 to 18 carbon atoms, and more preferably is alkyl of from 1 to 8 carbon atoms, and more preferably still of from 1 to 2 carbon atoms.

Another useful class of polymers is polymers prepared by cationic polymerization of monomers such as isobutene and styrene. Common polymers from this class include polyisobutenes obtained by polymerization of a $C_4$ refinery stream having a butene content of 35 to 75% by wt., and an isobutene content of 30 to 60% by wt. A preferred source of monomer for making poly-n-butenes is petroleum feedstreams such as Raffinate II. These feedstocks are disclosed in the art such as in U.S. Pat. No. 4,952,739. A preferred embodiment utilizes polyisobutylene prepared from a pure isobutylene stream or a Raffinate I stream to prepare reactive isobutylene polymers with terminal vinylidene olefins. Polyisobutene polymers that may be employed are generally based on a polymer chain of from 1500 to 3000.

The dispersant(s) are preferably non-polymeric (e.g., mono- or bis-succinimides). Such dispersants can be prepared by conventional processes such as disclosed in U.S. Patent Application Publication No. 2008/0020950, the disclosure of which is incorporated herein by reference.

The dispersant(s) can be borated by conventional means, as generally disclosed in U.S. Pat. Nos. 3,087,936, 3,254,025 and 5,430,105.

Such dispersants may be used in an amount of about 0.01 to 20 weight percent or 0.01 to 10 weight percent, preferably about 0.5 to 8 weight percent, or more preferably 0.5 to 4 weight percent. Or such dispersants may be used in an amount of about 2 to 12 weight percent, preferably about 4 to 10 weight percent, or more preferably 6 to 9 weight percent. On an active ingredient basis, such additives may be used in an amount of about 0.06 to 14 weight percent, preferably about 0.3 to 6 weight percent. The hydrocarbon portion of the dispersant atoms can range from $C_{60}$ to $C_{1000}$, or from $C_{70}$ to $C_{300}$, or from $C_{70}$ to $C_{200}$. These dispersants may contain both neutral and basic nitrogen, and mixtures of both. Dispersants can be end-capped by borates and/or cyclic carbonates.

As used herein, the dispersant concentrations are given on an "as delivered" basis. Typically, the active dispersant is delivered with a process oil. The "as delivered" dispersant typically contains from about 20 weight percent to about 80 weight percent, or from about 40 weight percent to about 60 weight percent, of active dispersant in the "as delivered" dispersant product.

Viscosity Modifiers

Viscosity modifiers (also known as viscosity index improvers (VI improvers), and viscosity improvers) can be included in the lubricant compositions of this disclosure.

Viscosity modifiers provide lubricants with high and low temperature operability. These additives impart shear stability at elevated temperatures and acceptable viscosity at low temperatures.

Suitable viscosity modifiers include high molecular weight hydrocarbons, polyesters and viscosity modifier dispersants that function as both a viscosity modifier and a dispersant. Typical molecular weights of these polymers are between about 10,000 to 1,500,000, more typically about 20,000 to 1,200,000, and even more typically between about 50,000 and 1,000,000.

Examples of suitable viscosity modifiers are linear or star-shaped polymers and copolymers of methacrylate, butadiene, olefins, or alkylated styrenes. Polyisobutylene is a commonly used viscosity modifier. Another suitable viscosity modifier is polymethacrylate (copolymers of various chain length alkyl methacrylates, for example), some formulations of which also serve as pour point depressants. Other suitable viscosity modifiers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

Olefin copolymers are commercially available from Chevron Oronite Company LLC under the trade designation "PARATONE®" (such as "PARATONE® 8921" and "PARATONE® 8941"); from Afton Chemical Corporation under the trade designation "HiTEC®" (such as "HiTEC® 5850B"; and from The Lubrizol Corporation under the trade designation "Lubrizol® 7067C". Hydrogenated polyisoprene star polymers are commercially available from Infineum International Limited, e.g., under the trade designation "SV200" and "SV600". Hydrogenated diene-styrene block copolymers are commercially available from Infineum International Limited, e.g., under the trade designation "SV 50".

The polymethacrylate or polyacrylate polymers can be linear polymers which are available from Evnoik Industries under the trade designation "Viscoplex®" (e.g., Viscoplex 6-954) or star polymers which are available from Lubrizol Corporation under the trade designation Asteric™ (e.g., Lubrizol 87708 and Lubrizol 87725).

Illustrative vinyl aromatic-containing polymers useful in this disclosure may be derived predominantly from vinyl aromatic hydrocarbon monomer. Illustrative vinyl aromatic-containing copolymers useful in this disclosure may be represented by the following general formula:

wherein A is a polymeric block derived predominantly from vinyl aromatic hydrocarbon monomer, and B is a polymeric block derived predominantly from conjugated diene monomer.

In an embodiment of this disclosure, the viscosity modifiers may be used in an amount of less than about 2.0 weight percent, preferably less than about 1.0 weight percent, and more preferably less than about 0.5 weight percent, based on the total weight of the formulated oil or lubricating engine or other mechanical component oil. Viscosity modifiers are typically added as concentrates, in large amounts of diluent oil.

As used herein, the viscosity modifier concentrations are given on an "as delivered" basis. Typically, the active polymer is delivered with a diluent oil. The "as delivered" viscosity modifier typically contains from 20 weight percent to 75 weight percent of an active polymer for polymethacrylate or polyacrylate polymers, or from 8 weight percent to 20 weight percent of an active polymer for olefin copolymers, hydrogenated polyisoprene star polymers, or hydrogenated diene-styrene block copolymers, in the "as delivered" polymer concentrate.

Antioxidants

Antioxidants retard the oxidative degradation of base oils during service. Such degradation may result in deposits on metal surfaces, the presence of sludge, or a viscosity increase in the lubricant. One skilled in the art knows a wide variety of oxidation inhibitors that are useful in lubricating oil compositions. See, Klamann in Lubricants and Related Products, op cite, and U.S. Pat. Nos. 4,798,684 and 5,084,197, for example.

Useful antioxidants include hindered phenols. These phenolic antioxidants may be ashless (metal-free) phenolic compounds or neutral or basic metal salts of certain phenolic compounds. Typical phenolic antioxidant compounds are the hindered phenolics which are the ones which contain a sterically hindered hydroxyl group, and these include those derivatives of dihydroxy aryl compounds in which the hydroxyl groups are in the o- or p-position to each other. Typical phenolic antioxidants include the hindered phenols substituted with $C_6$+ alkyl groups and the alkylene coupled derivatives of these hindered phenols. Examples of phenolic materials of this type 2-t-butyl-4-heptyl phenol; 2-t-butyl- 4-octyl phenol; 2-t-butyl-4-dodecyl phenol; 2,6-di-t-butyl-4-heptyl phenol; 2,6-di-t-butyl-4-dodecyl phenol; 2-methyl-6-t-butyl-4-heptyl phenol; and 2-methyl-6-t-butyl-4-dodecyl phenol. Other useful hindered mono-phenolic antioxidants may include for example hindered 2,6-di-alkyl-phenolic proprionic ester derivatives. Bis-phenolic antioxidants may also be advantageously used in combination with the instant disclosure. Examples of ortho-coupled phenols include: 2,2'-bis(4-heptyl-6-t-butyl-phenol); 2,2'-bis(4-octyl-6-t-butyl-phenol); and 2,2'-bis(4-dodecyl-6-t-butyl-phenol). Para-coupled bisphenols include for example 4,4'-bis(2,6-di-t-butyl phenol) and 4,4'-methylene-bis(2,6-di-t-butyl phenol).

Effective amounts of one or more catalytic antioxidants may also be used. The catalytic antioxidants comprise an effective amount of a) one or more oil soluble polymetal organic compounds; and, effective amounts of b) one or more substituted N,N'-diaryl-o-phenylenediamine compounds or c) one or more hindered phenol compounds; or a combination of both b) and c). Catalytic antioxidants are more fully described in U.S. Pat. No. 8,048,833, herein incorporated by reference in its entirety.

Non-phenolic oxidation inhibitors which may be used include aromatic amine antioxidants and these may be used either as such or in combination with phenolics. Typical examples of non-phenolic antioxidants include: alkylated and non-alkylated aromatic amines such as aromatic mono-amines of the formula $R^8R^9R^{10}N$ where $R^8$ is an aliphatic, aromatic or substituted aromatic group, $R^9$ is an aromatic or a substituted aromatic group, and $R^{10}$ is H, alkyl, aryl or $R^{11}S(O)_xR^{12}$ where $R^{11}$ is an alkylene, alkenylene, or aralkylene group, $R^{12}$ is a higher alkyl group, or an alkenyl, aryl, or alkaryl group, and x is 0, 1 or 2. The aliphatic group $R^8$ may contain from 1 to about 20 carbon atoms, and preferably contains from about 6 to 12 carbon atoms. The aliphatic group is a saturated aliphatic group. Preferably, both $R^8$ and $R^9$ are aromatic or substituted aromatic groups, and the aromatic group may be a fused ring aromatic group such as naphthyl. Aromatic groups $R^8$ and $R^9$ may be joined together with other groups such as S.

Typical aromatic amines antioxidants have alkyl substituent groups of at least about 6 carbon atoms. Examples of aliphatic groups include hexyl, heptyl, octyl, nonyl, and decyl. Generally, the aliphatic groups will not contain more than about 14 carbon atoms. The general types of amine antioxidants useful in the present compositions include diphenylamines, phenyl naphthylamines, phenothiazines, imidodibenzyls and diphenyl phenylene diamines. Mixtures of two or more aromatic amines are also useful. Polymeric amine antioxidants can also be used. Particular examples of aromatic amine antioxidants useful in the present disclosure include: p,p'-dioctyldiphenylamine; t-octylphenyl-alpha-naphthylamine; phenyl-alphanaphthylamine; and p-octyl-phenyl-alpha-naphthylamine.

Sulfurized alkyl phenols and alkali or alkaline earth metal salts thereof also are useful antioxidants.

Preferred antioxidants include hindered phenols, arylamines. These antioxidants may be used individually by type or in combination with one another. Such additives may be used in an amount of about 0.01 to 5 weight percent, preferably about 0.01 to 1.5 weight percent, more preferably zero to less than 1.5 weight percent, more preferably zero to less than 1 weight percent.

Pour Point Depressants (PPDs)

Conventional pour point depressants (also known as lube oil flow improvers) may be added to the compositions of the present disclosure if desired. These pour point depressant may be added to lubricating compositions of the present disclosure to lower the minimum temperature at which the fluid will flow or can be poured. Examples of suitable pour point depressants include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655, 479; 2,666,746; 2,721,877; 2,721,878; and 3,250,715 describe useful pour point depressants and/or the preparation thereof. Such additives may be used in an amount of about 0.01 to 5 weight percent, preferably about 0.01 to 1.5 weight percent.

Seal Compatibility Agents

Seal compatibility agents help to swell elastomeric seals by causing a chemical reaction in the fluid or physical change in the elastomer. Suitable seal compatibility agents for lubricating oils include organic phosphates, aromatic esters, aromatic hydrocarbons, esters (butylbenzyl phthalate, for example), and polybutenyl succinic anhydride. Such additives may be used in an amount of about 0.01 to 3 weight percent, preferably about 0.01 to 2 weight percent.

Antifoam Agents

Anti-foam agents may advantageously be added to lubricant compositions. These agents retard the formation of stable foams. Silicones and organic polymers are typical anti-foam agents. For example, polysiloxanes, such as silicon oil or polydimethyl siloxane, provide antifoam properties. Anti-foam agents are commercially available and may be used in conventional minor amounts along with other additives such as demulsifiers; usually the amount of these additives combined is less than 1 weight percent and often less than 0.1 weight percent.

Inhibitors and Antirust Additives

Antirust additives (or corrosion inhibitors) are additives that protect lubricated metal surfaces against chemical attack by water or other contaminants. A wide variety of these are commercially available.

One type of antirust additive is a polar compound that wets the metal surface preferentially, protecting it with a film of oil. Another type of antirust additive absorbs water by incorporating it in a water-in-oil emulsion so that only the oil touches the metal surface. Yet another type of antirust additive chemically adheres to the metal to produce a non-reactive surface. Examples of suitable additives include zinc dithiophosphates, metal phenolates, basic metal sulfonates, fatty acids and amines. Such additives may be used in an amount of about 0.01 to 5 weight percent, preferably about 0.01 to 1.5 weight percent.

Friction Modifiers

A friction modifier is any material or materials that can alter the coefficient of friction of a surface lubricated by any lubricant or fluid containing such material(s). Friction modifiers, also known as friction reducers, or lubricity agents or oiliness agents, and other such agents that change the ability of base oils, formulated lubricant compositions, or functional fluids, to modify the coefficient of friction of a lubricated surface may be effectively used in combination with the base oils or lubricant compositions of the present disclosure if desired. Friction modifiers that lower the coefficient of friction are particularly advantageous in combination with the base oils and lube compositions of this disclosure.

Illustrative friction modifiers may include, for example, organometallic compounds or materials, or mixtures thereof. Illustrative organometallic friction modifiers useful in the lubricating engine or other mechanical component oil formulations of this disclosure include, for example, molybdenum amine, molybdenum diamine, an organotungstenate, a molybdenum dithiocarbamate, molybdenum dithiophosphates, molybdenum amine complexes, molybdenum carboxylates, and the like, and mixtures thereof. Similar tungsten based compounds may be preferable.

Other illustrative friction modifiers useful in the lubricating engine or other mechanical component oil formulations of this disclosure include, for example, alkoxylated fatty acid esters, alkanolamides, polyol fatty acid esters, borated glycerol fatty acid esters, fatty alcohol ethers, and mixtures thereof.

Illustrative alkoxylated fatty acid esters include, for example, polyoxyethylene stearate, fatty acid polyglycol ester, and the like. These can include polyoxypropylene stearate, polyoxybutylene stearate, polyoxyethylene isosterate, polyoxypropylene isostearate, polyoxyethylene palmitate, and the like.

Illustrative alkanolamides include, for example, lauric acid diethylalkanolamide, palmic acid diethylalkanolamide, and the like. These can include oleic acid diethylalkanolamide, stearic acid diethylalkanolamide, oleic acid diethylalkanolamide, polyethoxylated hydrocarbylamides, polypropoxylated hydrocarbylamides, and the like.

Illustrative polyol fatty acid esters include, for example, glycerol mono-oleate, saturated mono-, di-, and tri-glyceride esters, glycerol mono-stearate, and the like. These can include polyol esters, hydroxyl-containing polyol esters, and the like.

Illustrative borated glycerol fatty acid esters include, for example, borated glycerol mono-oleate, borated saturated mono-, di-, and tri-glyceride esters, borated glycerol monostearate, and the like. In addition to glycerol polyols, these can include trimethylolpropane, pentaerythritol, sorbitan, and the like. These esters can be polyol monocarboxylate esters, polyol dicarboxylate esters, and on occasion polyoltricarboxylate esters. Preferred can be the glycerol monooleates, glycerol dioleates, glycerol trioleates, glycerol monostearates, glycerol distearates, and glycerol tristearates and the corresponding glycerol monopalmitates, glycerol dipalmitates, and glycerol tripalmitates, and the respective isostearates, linoleates, and the like. On occasion the glycerol esters can be preferred as well as mixtures containing any of these. Ethoxylated, propoxylated, butoxylated fatty acid esters of polyols, especially using glycerol as underlying polyol can be preferred.

Illustrative fatty alcohol ethers include, for example, stearyl ether, myristyl ether, and the like. Alcohols, including those that have carbon numbers from $C_3$ to $C_{50}$, can be ethoxylated, propoxylated, or butoxylated to form the corresponding fatty alkyl ethers. The underlying alcohol portion can preferably be stearyl, myristyl, $C_{11}$-$C_{13}$ hydrocarbon, oleyl, isosteryl, and the like.

The lubricating oils of this disclosure exhibit desired properties, e.g., wear control, in the presence or absence of a friction modifier.

Useful concentrations of friction modifiers may range from 0.01 weight percent to 5 weight percent, or about 0.1 weight percent to about 2.5 weight percent, or about 0.1 weight percent to about 1.5 weight percent, or about 0.1 weight percent to about 1 weight percent. Concentrations of molybdenum-containing materials are often described in terms of Mo metal concentration. Advantageous concentrations of Mo may range from 25 ppm to 700 ppm or more, and often with a preferred range of 50-200 ppm. Friction modifiers of all types may be used alone or in mixtures with the materials of this disclosure. Often mixtures of two or more friction modifiers, or mixtures of friction modifier(s) with alternate surface active material(s), are also desirable.

When lubricating oil compositions contain one or more of the additives discussed above, the additive(s) are blended into the composition in an amount sufficient for it to perform its intended function. Typical amounts of such additives useful in the present disclosure are shown in Table 1 below.

It is noted that many of the additives are shipped from the additive manufacturer as a concentrate, containing one or more additives together, with a certain amount of base oil diluents. Accordingly, the weight amounts in the table below, as well as other amounts mentioned herein, are directed to the amount of active ingredient (that is the non-diluent portion of the ingredient). The weight percent (wt %) indicated below is based on the total weight of the lubricating oil composition.

TABLE 1

Typical Amounts of Other Lubricating Oil Components

| Compound | Approximate wt % (Useful) | Approximate wt % (Preferred) |
|---|---|---|
| Dispersant | 0.1-20 | 0.1-8 |
| Detergent | 0.1-20 | 0.1-8 |
| Friction Modifier | 0.01-5 | 0.01-1.5 |
| Antioxidant | 0.1-5 | 0.1-1.5 |
| Pour Point Depressant (PPD) | 0.0-5 | 0.01-1.5 |
| Anti-foam Agent | 0.001-3 | 0.001-0.15 |
| Viscosity Modifier (solid polymer basis) | 0.1-2 | 0.1-1 |
| Antiwear | 0.2-3 | 0.5-1 |
| Inhibitor and Antirust | 0.01-5 | 0.01-1.5 |

The foregoing additives are all commercially available materials. These additives may be added independently but are usually precombined in packages which can be obtained from suppliers of lubricant oil additives. Additive packages with a variety of ingredients, proportions and characteristics are available and selection of the appropriate package will take the requisite use of the ultimate composition into account.

The following non-limiting examples are provided to illustrate the disclosure.

EXAMPLES

Formulations were prepared as described herein. All of the ingredients used herein, except the phosphazenes of this disclosure, are commercially available. PCMO (passenger car motor oil) formulations were prepared as described herein.

The phosphazene antiwear additive used in the formulations was (propylamino-co-butylamino)cyclotriphosphazene represented by the formula

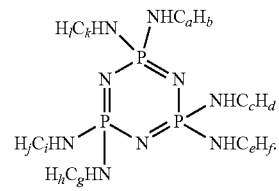

wherein the substituents were propyl and butyl amino groups in a ratio of 2.44:3.56.

The additive package used in the formulations included conventional additives in conventional amounts. Conventional additives used in the formulations were one or more of an antiwear additive, detergent, antioxidant, dispersant, pour point depressant, corrosion inhibitor, metal deactivator, seal compatibility additive, anti-foam agent, inhibitor, anti-rust additive, and friction modifier.

A tribometer was used for measuring wear. A ball was held in a reciprocating arm so that it was brought into contact with a flat disk. The flat disk and the ball were positioned inside a lubricant reservoir and sufficient lubricant is placed in the reservoir to cover the contact point between ball and disk. The reciprocating arm was reciprocated back and forth while maintaining contact between the ball and disk. A variable weight was hung over the reciprocating arm thus allowing wear to be measured under different load conditions. In addition, the stroke length of the reciprocating arm can be varied as was the oil reservoir temperature. Friction was measured with a load cell attached to the reciprocating arm.

Wear performance was evaluated as described above using a High Frequency Reciprocating Rig (HFRR) test. The HFRR is commercially available from PCS Industries. The test equipment and procedure are similar to the ASTM D6079 method. The HFRR test conditions were as follows: temperature 100° C.; test duration 2 hours; stroke length 1 mm; frequency 10 Hz; and load 400 grams. Wear was measured only on the disc. The ball and disk are commercially available from PCS Industries. The ball and disk are both 52100 steel. The disks are 200 HV hardened.

The lubricant formulations used in the Examples are shown in Table 2 below. The weight percent (wt %) indicated below is based on the total weight of the lubricating oil composition.

TABLE 2

| Lubricant<br>Component Description | Partial Formulation<br>(wt %) | Full Formulation<br>(wt %) |
| --- | --- | --- |
| Synthetic Base Oil Mixture | 82.5-91.5 | 80.5-89.5 |
| Viscosity Modifier | 0-5 | 0-5 |
| Performance Additives System | 9-10 | 9-10 |
| ZDDP & Friction Modifiers | 0 | 2 |
| Additive of this Disclosure | 0-1.5 | 0 |

Example 1

Synthesis of Phosphazene of Formula 1

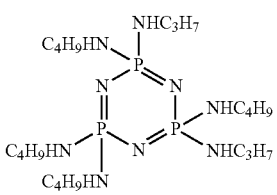

A mixture of 1-propylamine (421 mL, 5.13 mol) and 1-butylamine (601 mL, 6.08 mol) was added to a solution of hexachlorocyclotriphosphazene (556 g, 1.60 mol) and triethylamine (1.78 L, 12.7 mol) in 6.4 L dichloromethane dropwise at 0° C. The mixture was stirred at ambient temperature for 2 days. The reaction mixture was washed with 2 L water, 2 L 5% HCl, and 2 L 5% NaOH twice, dried over anhydrous $Na_2SO_4$, concentrated and dried under high vacuum to yield a yellowish waxy solid (800 g, 94%).

Example 2

Synthesis of Phosphazene of Formula 2

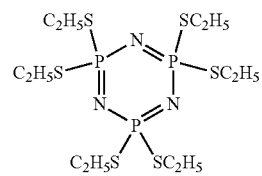

Ethanethiol (10.1 mL, 0.140 mol) was added to a suspension of sodium hydride (60% dispersion in mineral oil, 5.60 g, 0.140 mol) in 250 mL THF dropwise at 0° C. The reaction mixture was stirred at ambient temperature over night. To the resulting white suspension was added hexachlorocyclotriphosphazene (6.95 g, 20.0 mmol) portionwise at 0° C. The mixture was stirred at ambient temperature for 1 day and then heated to reflux and stirred for one additional day. Most of the solvent was removed by rotary evaporation. The residue was redissolved in 200 mL DCM, washed with 50 mL 5% NaOH, dried over anhydrous $Na_2SO_4$, concentrated liquid, purified by silica gel column with ethyl acetate/hexane=40/1 (v/v) as eluent to yield a colorless liquid (8.15 g, 81%).

Example 3

Synthesis of Phosphazene of Formula 3

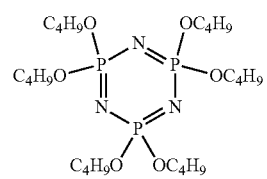

Sodium hydride (60% dispersion in mineral oil, 15.0 g, 0.375 mol) was washed with 50 mL anhydrous diethyl ether twice to remove mineral oil and was then suspended in 300 mL THF. 1-butanol (34.3 mL, 0.375 mol) was added to the suspension dropwise at 0° C. The reaction mixture was stirred at ambient temperature for 2 hours. To the resulting white suspension was added hexachlorocyclotriphosphazene (17.4 g, 50.0 mmol) portionwise at 0° C. The mixture was stirred at ambient temperature for 1 day and then heated to reflux and stirred for one additional day. Most of the solvent was removed by rotary evaporation. The residue was redissolved in 500 mL DCM, washed with 100 mL 5% HCl and 100 mL saturated $NaHCO_3$ solution successively, dried over anhydrous $Na_2SO_4$, concentrated and dried under high vacuum to yield a yellowish liquid (27.8 g, 97%).

Example 4

A phosphazene was blended into polyalphaolefin (PAO 4) and tested in the HFRR. This wear test run was compared to a wear test run on PAO 4 containing no additives. During the two hour duration of the HFRR test a continuous measurement of friction between the ball and flat cylinder was made. While friction changed during the duration of the test, the friction measurement used herein was the average friction during the last half hour of the test procedure. This number is referred to as the average friction. After the HFRR test was completed, the ball and disk were removed from the tribometer. The topography (i.e., depth profile) of the wear scar produced at the center of the disk was measured with a profilimeter. The depth of the elongated wear scar was measured along three lines across the wear scar. One profile was generated across the center of the wear scar, a second and third were measured to the right and left of the wear scar center line. A single wear scar depth number was generated by taking the average depth achieved at the center of each of the three profiles and averaging them.

The wear scar depth for the phosphazene containing fluid is tabulated below and compared to the wear scar depth for the PAO test. The data shows that (propylamino-co-butylamino)cyclotriphosphazene represented by the formula 1

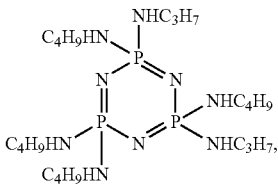

reduced wear when added to the lubricant base stock.

Other phosphazenes tested included substituted phosphazene trimers where the substituents were alcohols and mercaptans. A thiol substituted trimer was tested that is represented by the formula 2

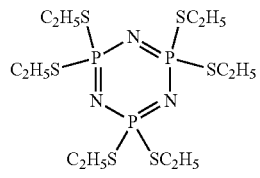

An alcohol substituted trimer was also tested that is represented by the formula 3

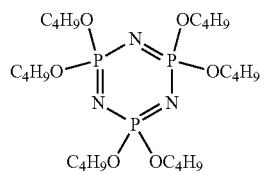

Each phosphazene additive of formulae 1, 2 and 3 was evaluated by blending 1.5 weight percent of the phosphazene into a reference formula containing a full complement of passenger vehicle lubricant additives without ZDDP and friction modifier. This reference formula is known as the "partial" formulation and represents performance in the absence of antiwear additives. A reference test was also run on this formulation including friction modifier and ZDDP ("full formulation"). This represents the performance of a high performing lubricant. HFRR data (i.e., average friction and wear scar depth) are tabulated in the table in FIG. 1.

The data in FIG. 1 shows that the formula 1 phosphazene reduced wear when added to the lubricant base stock, was the overall highest performing additive, and was optimized for solubility in polyalphaolefin (PAO) basestock by using a mixture of butyl and propyl side groups.

Solubility was improved by using the mixed butyl/propyl molecule shown as formula 1 phosphazene. Phosphazenes are polymers consisting of a backbone comprising alternating sulfur and phosphorous units. A trimer has 3 P—N repeating units and is believed to form a six membered ring. Each pentavalent phosphorous can have two additional substituents. In the case of a phosphazene of formula 1, there is a mixture of propyl and butyl amino groups in a ratio of 2.44:3.56.

In the HFRR test data shown in FIG. 1, the phosphazenes of formulae 1, 2 and 3 (especially the phosphazene of formula 1) performed better than a lubricant formulated with ZDDP, the most common commercially used antiwear additive. While the phosphazene of formula 1 contains phosphorous, it is free of metals and sulfur which are known to damage exhaust aftertreatment systems. Reduced sulfur may provide an additional performance advantage for sulfur free phosphazenes.

The lubricants of this disclosure are low in sulfur and are less corrosive than antiwear additives containing sulfur. One manifestation of this is that the present disclosure is less likely to corrode ferrous materials (e.g., steel) to produce iron sulfide.

PCT and EP Clauses:

1. A method for improving wear control in an engine or other mechanical component lubricated with a lubricating oil by using as the lubricating oil a formulated oil, said formulated oil having a composition comprising a lubricating oil base stock as a major component; and at least one phosphazene represented by the formula

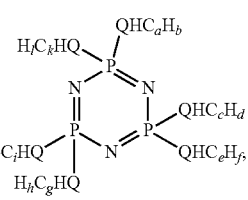

as a minor component; wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of $2a+q$, d is a value of $2c+r$, f is a value of $2e+s$, h is a value of $2g+t$, j is a value of $2i+u$, and l is a value of $2k+v$; q, r, s, t, u and v are independently a value of 0 or −2; with the proviso that not all of a, c, e, g, i and k are the same value; and wherein wear control is improved as compared to wear control achieved using a lubricating oil containing a minor component other than the phosphazene.

2. The method of clause 1 wherein a, c, e, g, i and k are a value of 3 (propyl) or 4 (butyl), and wherein the ratio of propyl to butyl groups is between 1:10 and 10:1.

3. The method of clauses 1 and 2 wherein the at least one phosphazene is present in an amount of from 0.01 weight percent to 5 weight percent, based on the total weight of the formulated oil.

4. The method of clauses 1-3 wherein the lubricating oil base stock is present in an amount of from 70 weight percent to 95 weight percent, based on the total weight of the formulated oil.

5. The method of clauses 1-4 wherein the phosphazene is represented by the formula

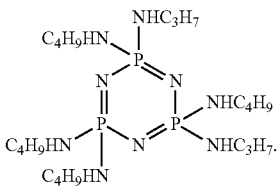

6. The method of clauses 1-5 wherein the phosphazene is present in an amount less than 1 weight percent, based on the total weight of the formulated oil.

7. A lubricating oil having a composition comprising a lubricating oil base stock as a major component; and at least one phosphazene represented by the formula

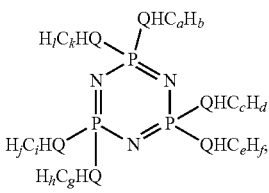

as a minor component; wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein wear control is improved as compared to wear control achieved using a lubricating oil containing a minor component other than the phosphazene.

8. The lubricating oil of clause 7 wherein a, c, e, g, i and k are a value of 3 (propyl) or 4 (butyl), and wherein the ratio of propyl to butyl groups is between 1:10 and 10:1.

9. The lubricating oil of clauses 7 and 8 wherein the at least one phosphazene is present in an amount of from 0.01 weight percent to 5 weight percent, based on the total weight of the formulated oil; and wherein the lubricating oil base stock is present in an amount of from 70 weight percent to 95 weight percent, based on the total weight of the formulated oil.

10. The lubricating oil of clauses 7-9 wherein the phosphazene is represented by the formula

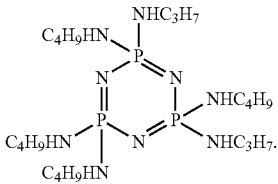

11. A composition represented by the formula

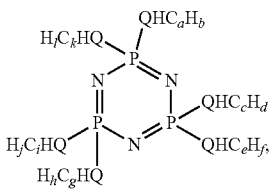

wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value.

12. A process for preparing a composition represented by the formula

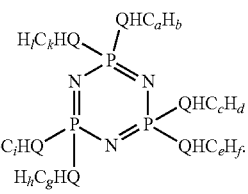

wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; said process comprising: reacting one or more alkylamines, thiols or alcohols and one or more phosphazene precursors in the presence of a solvent and under reaction conditions sufficient to prepare the composition represented by the above formula.

13. A method for reducing sulfur and metals and their harmful side effects of exhaust catalyst poisoning and increased corrosivity in an engine or other mechanical component lubricated with a lubricating oil by including at least one phosphazene represented by the formula

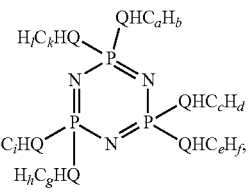

in the lubricating oil; wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein the at least one phosphazene is present in an amount from 0.01 weight percent to 2 weight percent, based on the total weight of the lubricating oil.

14. A low sulfur, low metal lubricating oil having a composition comprising a lubricating oil base stock as a major component, and at least one phosphazene represented by the formula

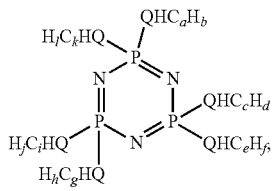

as a minor component; wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value and wherein the at least one phosphazene is present in an amount from 0.01 weight percent to 2 weight percent, based on the total weight of the lubricating engine or other mechanical component oil.

15. A method for producing a stable lubricating oil formulation with improved wear control in an engine or other mechanical component lubricated with a lubricating oil by using as the lubricating oil a formulated oil; wherein the formulated oil has a composition comprising a lubricating oil base stock as a major component; and at least one phosphazene represented by the formula

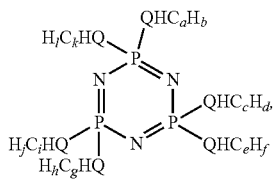

as a minor component; wherein Q is nitrogen, sulfur or oxygen; a is a value from 2 to 6, c is a value from 2 to 6, e is a value from 2 to 6, g is a value from 2 to 6, i is a value from 2 to 6, and k is a value from 2 to 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein wear control is improved as compared to wear control achieved using a lubricating oil containing a minor component other than the phosphazene.

All patents and patent applications, test procedures (such as ASTM methods, UL methods, and the like), and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated. While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

The present disclosure has been described above with reference to numerous embodiments and specific examples. Many variations will suggest themselves to those skilled in this art in light of the above detailed description. All such obvious variations are within the full intended scope of the appended claims.

What is claimed is:

1. A method for improving wear control in an engine or other mechanical component lubricated with a lubricating oil by using as the lubricating oil a formulated oil, said formulated oil having a composition comprising a lubricating oil base stock as a major component; and at least one phosphazene represented by the formula

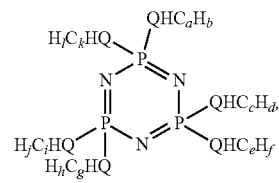

as a minor component; wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein wear control is improved as compared to wear control achieved using a lubricating oil containing a minor component other than the phosphazene, wherein the other mechanical component is selected from the group consisting of power trains, drivelines, transmissions, gears, gear trains, gear sets, compressors, pumps, hydraulic systems, bearings, bushings and turbines.

2. The method of claim 1 wherein a, c, e, g, i and k are a value of 3 (propyl) or 4 (butyl).

3. The method of claim 1 wherein the phosphazene is represented by the formula

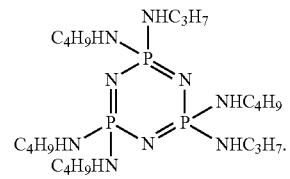

4. The method of claim 1 wherein the lubricating oil base stock comprises a Group I, Group II, Group III, Group IV or Group V base oil.

5. The method of claim 1 wherein the at least one phosphazene is present in an amount of from about 0.01 weight percent to about 5 weight percent, based on the total weight of the formulated oil.

6. The method of claim 1 wherein the phosphazene is present in an amount less than about 2 weight percent, based on the total weight of the formulated oil.

7. The method of claim 1 wherein the phosphazene is present in an amount less than about 1 weight percent, based on the total weight of the formulated oil.

8. The method of claim 1 wherein the lubricating oil base stock is present in an amount of from about 70 weight percent to about 95 weight percent, based on the total weight of the formulated oil.

9. The method of claim 1 wherein the formulated oil further comprises one or more of an antiwear additive, viscosity modifier, antioxidant, detergent, dispersant, pour point depressant, corrosion inhibitor, metal deactivator, seal compatibility additive, anti-foam agent, inhibitor, and anti-rust additive.

10. A lubricating oil having a composition comprising a lubricating oil base stock as a major component; and at least one phosphazene represented by the formula

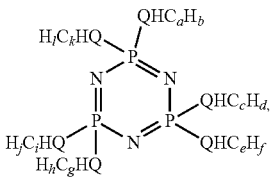

as a minor component; wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein wear control is improved as compared to wear control achieved using a lubricating oil containing a minor component other than the phosphazene.

11. The lubricating oil of claim 10 wherein a, c, e, g, i and k are a value of 3 (propyl) or 4 (butyl).

12. The lubricating oil of claim 10 wherein the phosphazene is represented by the formula

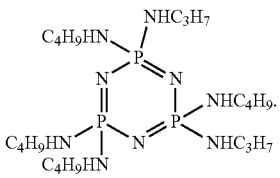

13. The lubricating oil of claim 10 wherein the lubricating oil base stock comprises a Group I, Group II, Group III, Group IV or Group V base oil.

14. The lubricating oil of claim 10 wherein the at least one phosphazene is present in an amount of from about 0.01 weight percent to about 5 weight percent, based on the total weight of the formulated oil.

15. The lubricating oil of claim 10 wherein the phosphazene is present in an amount less than about 2 weight percent, based on the total weight of the formulated oil.

16. The lubricating oil of claim 10 wherein the phosphazene is present in an amount less than about 1 weight percent, based on the total weight of the formulated oil.

17. The lubricating oil of claim 10 wherein the lubricating oil base stock is present in an amount of from about 70 weight percent to about 95 weight percent, based on the total weight of the formulated oil.

18. The lubricating oil of claim 10 further comprising one or more of an antiwear additive, viscosity modifier, antioxidant, detergent, dispersant, pour point depressant, corrosion inhibitor, metal deactivator, seal compatibility additive, anti-foam agent, inhibitor, and anti-rust additive.

19. The lubricating oil of claim 10 which is a passenger vehicle engine oil (PVEO).

20. A method for reducing sulfur and metals and their harmful side effects of exhaust catalyst poisoning and increased corrosivity in an engine or other mechanical component lubricated with a lubricating oil by including at least one phosphazene represented by the formula

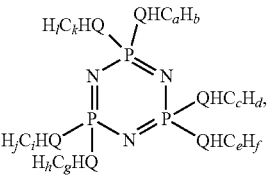

in the lubricating oil; wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein the at least one phosphazene is present in an amount from about 0.01 weight percent to about 2 weight percent, based on the total weight of the lubricating oil, wherein the other mechanical component is selected from the group consisting of power trains, drivelines, transmissions, gears, gear trains, gear sets, compressors, pumps, hydraulic systems, bearings, bushings and turbines.

21. The method of claim 20 wherein a, c, e, g, i and k are a value of 3 (propyl) or 4 (butyl).

22. The method of claim 20 wherein the phosphazene is represented by the formula

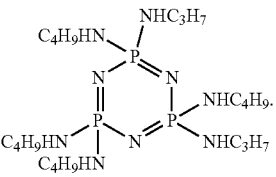

23. A lubricating oil having a composition comprising a lubricating oil base stock as a major component, and at least one phosphazene represented by the formula

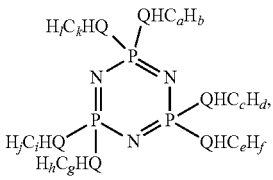

as a minor component; wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value and wherein the at least one phosphazene is present in an amount from about 0.01 weight percent to about 2 weight percent, based on the total weight of the lubricating oil.

24. The lubricating oil of claim 23 wherein a, c, e, g, i and k are a value of 3 (propyl) or 4 (butyl).

25. The lubricating oil of claim 23 wherein the phosphazene is represented by the formula

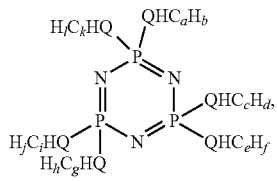

26. The method of claim 1 wherein the formulated oil further comprises an antiwear additive, wherein the antiwear additive comprises zinc dialkyl dithio phosphate (ZDDP), and wherein the ZDDP is present in an amount less than about 0.80 weight percent.

27. The method of claim 1 wherein said formulated oil further includes zinc dialkyl dithio phosphate (ZDDP) present in an amount less than about 0.40 weight percent.

28. The method of claim 27 wherein the ZDDP is present in an amount less than about 0.20 weight percent.

29. The lubricating oil of claim 10 further comprising an antiwear additive, wherein the antiwear additive comprises zinc dialkyl dithio phosphate (ZDDP), and wherein the ZDDP is present in an amount less than about 0.80 weight percent.

30. The lubricating oil of claim 10 wherein the lubricating oil further includes zinc dialkyl dithio phosphate (ZDDP) present in an amount less than about 0.40 weight percent.

31. The lubricating oil of claim 30 wherein the ZDDP is present in an amount less than about 0.20 weight percent.

32. A method for producing a stable lubricating oil formulation with improved wear control in an engine or other mechanical component lubricated with a lubricating oil by using as the lubricating oil a formulated oil; wherein the formulated oil has a composition comprising a lubricating oil base stock as a major component; and at least one phosphazene represented by the formula

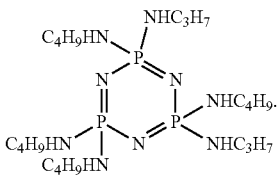

as a minor component; wherein Q is nitrogen, sulfur or oxygen; a is a value from about 2 to about 6, c is a value from about 2 to about 6, e is a value from about 2 to about 6, g is a value from about 2 to about 6, i is a value from about 2 to about 6, and k is a value from about 2 to about 6; b is a value of 2a+q, d is a value of 2c+r, f is a value of 2e+s, h is a value of 2g+t, j is a value of 2i+u, and l is a value of 2k+v; q, r, s, t, u and v are independently a value of 0 or −2; with the proviso that not all of a, c, e, g, i and k are the same value; and wherein wear control is improved as compared to wear control achieved using a lubricating oil containing a minor component other than the phosphazene, wherein the other mechanical component is selected from the group consisting of power trains, drivelines, transmissions, gears, gear trains, gear sets, compressors, pumps, hydraulic systems, bearings, bushings and turbines.

* * * * *